(12) United States Patent
Lange et al.

(10) Patent No.: US 7,629,456 B2
(45) Date of Patent: Dec. 8, 2009

(54) MODIFIED L-NUCLEIC ACID

(75) Inventors: Christian Lange, Berlin (DE); Bernd Eschgfäller, Basel (CH); Sven Klussmann, Berlin (DE)

(73) Assignee: NOXXON Pharma AG, Berlin (DE)

( * ) Notice: Subject to any disclaimer, the term of this patent is extended or adjusted under 35 U.S.C. 154(b) by 775 days.

(21) Appl. No.: 10/493,569

(22) PCT Filed: Oct. 25, 2002

(86) PCT No.: PCT/EP02/11950

§ 371 (c)(1),
(2), (4) Date: Jul. 25, 2005

(87) PCT Pub. No.: WO03/035665

PCT Pub. Date: May 1, 2003

(65) Prior Publication Data

US 2006/0003326 A1    Jan. 5, 2006

(30) Foreign Application Priority Data

Oct. 26, 2001 (EP) .................................. 01125630
Aug. 1, 2002 (EP) .................................. 02017300

(51) Int. Cl.
*C07H 21/04* (2006.01)
*C07H 21/00* (2006.01)
*A61K 31/70* (2006.01)

(52) U.S. Cl. .................... 536/24.5; 536/23.1; 536/25.3; 514/44

(58) Field of Classification Search ........................ None
See application file for complete search history.

(56) References Cited

U.S. PATENT DOCUMENTS 6,051,698 A * 4/2000 Janjic et al. .............. 536/24.31

FOREIGN PATENT DOCUMENTS

WO    WO 94/20523 A1    9/1994
WO    WO 98/08856 A1    3/1998

OTHER PUBLICATIONS

Klussmann et al. Nature Biotechnology 1996, vol. 14, pp. 1112-1115.*
Nolte et al. Nature Biotechnology 1996, vol. 14, pp. 1116-1119.*
Opalinska et al. Nature Reviews Drug Discovery 2002, vol. 1, pp. 503-514.*
Asseline, U. et al. "Synthesis and Physicochemical Properties of Oligonucleotides Built with Either Alpha-L or Beta-L Nucleotides Units and Covalently Linked to an Acridine Derivative", Nucleic Acids Research, vol. 19, No. 15, Oxford University Press, XP002920044, Aug. 1991, pp. 4067-4074.
Moyroud, E. et al. "Synthesis and Enzymatic Digestion of an RNA Nonamer in Both Enantiomeric Forms", Tetrahedron, Elsevier Science Publishers, XP004203025, Amsterdam, NL, Mar. 2000, pp. 1475-1484.

* cited by examiner

*Primary Examiner*—Tracy Vivlemore
(74) *Attorney, Agent, or Firm*—MDIP LLC

(57) ABSTRACT

The present invention relates to a modified L-nucleic acid, comprising a L-nucleic acid part and a non-L-nucleic acid part, whereby the L-nucleic acid part is conjugated to the non-L-nucleic acid part and the conjugation of the L-nucleic acid part with the non-L-nucleic acid past leads to a slowed elimination out of the organism, in comparison with a L-nucleic acid which only comprises the L-nucleic acid part, said L-nucleic acid part being a spiegelmer.

20 Claims, 29 Drawing Sheets

Hexylamine linker

Maleimide + sulphide

Epoxide + amine

Epoxide + thiol

Isothiocyanate + amine

R = H, CH₃, Alkyl

Isocyanate + amine

PEG—N=C=O + HRN - linker - oligo → PEG—N(H)—C(=O)—NR—linker - oligo

R = H, CH₃, Alkyl

Fig. 17

Isocyanate + alcohol

PEG—N=C=O + HO - (linker) - oligo → PEG—N(H)—C(=O)—O—(linker)- oligo

Fig. 18

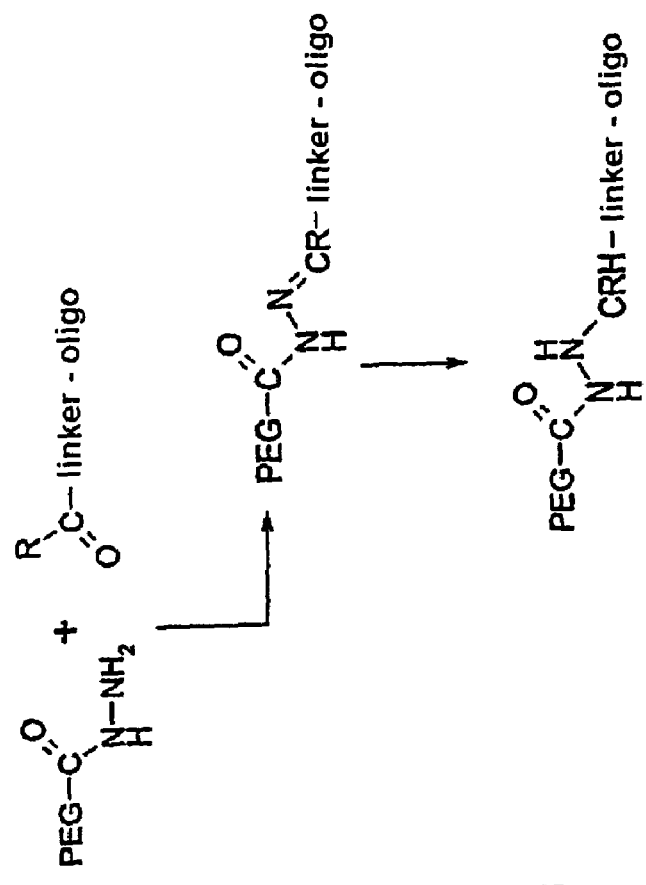

Structure linear and branched methoxy polyethylene glycol
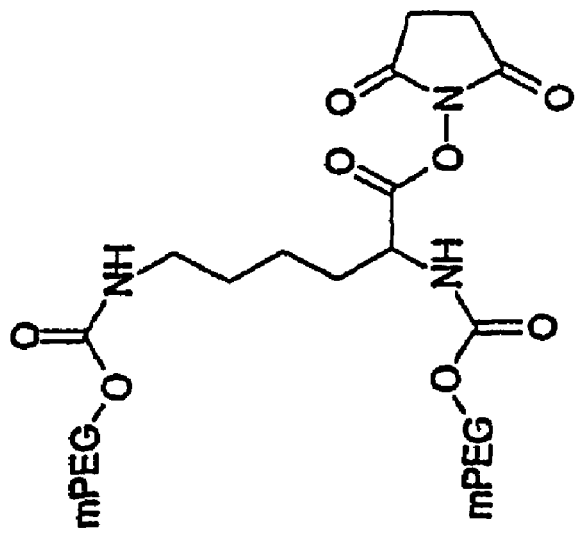
Fig. 23
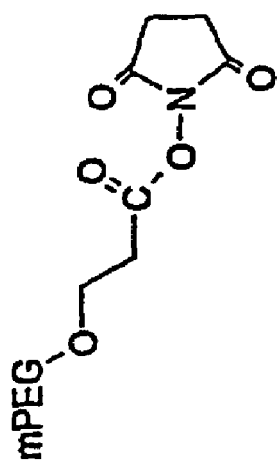

Abasic L-nucleoside
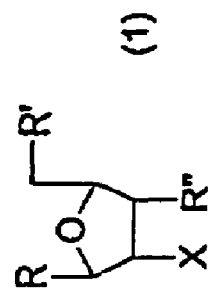
(1)
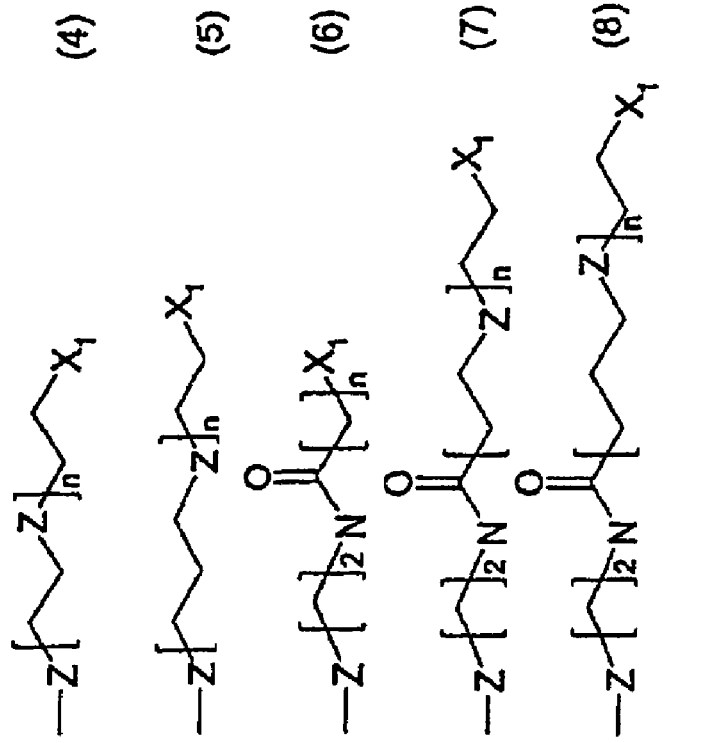
R' = HO, phosphate, oligo
R'' = HO, phosphate, oligo
X = H, OH, OMe, OEt, NH$_2$
X$_1$ = HO, H$_2$N, HRN, HS, SSR,
Hal, CHO, COOH, COOR, COHal
Z = CH$_2$, O, NH, NAlkyl, S
n = 1-20
Fig. 24

SEQUENCE LISTING

<160> NUMBER OF SEQ ID NOS: 7

<210> SEQ ID NO 1
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccaagcttgc gtaagcagtc tcctctcagg ggaggttggg cggtgcgtaa gcaccggttt      60
gcagggg                                                               67

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tattagagac                                                            10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tattagagac                                                            10

<210> SEQ ID NO 4
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uaaggaaacu cggucugaug cgguagcgcu gugcagagcu                           40

<210> SEQ ID NO 5
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5

```
uaaggaaacu cggucugaug cgguagcgcu gugcagagcu                          40

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: C-term amidated

<400> SEQUENCE: 6
ccgcatcaga ccgagtttcc ttattttttt tt                                 32

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Biotinylated at the 5' end

<400> SEQUENCE: 7 tttttttag ctctgcacag cgct                                           24
```

MODIFIED L-NUCLEIC ACID

The present invention relates to modified L-nucleic acids, their use, as well as to methods for their preparation.

Besides the use of comparatively small organic molecules the development of novel therapeutic concepts resorts increasingly to monoclonal antibodies, peptides and functional nucleic acids, i.e. such nucleic acids, that bind specifically to a target structure. Typical exponents of these functional nucleic acids are the so called aptamers, that have already been developed against a multitude of different biomolecules. Thereby, starting from a D-nucleic acid library, one or more nucleic acid molecules, the so called aptamers, that are distinguished by a particularly high affinity towards their target structure are isolated in several steps by in vitro selection. Methods for the preparation of such aptamers are described, for example, in European patent application EP 0 533 838.

In pharmacology the problem of stability and biological availability, expressed as the biological half time of the administered pharmaceutically active agents is sufficiently well known. Strategies to achieve a biological half time that permits the optimal effect of the administered pharmaceutically active substances concentrate on one hand on an appropriate modification of the pharmaceutically active agents and on the other hand on the development of appropriate forms of administration. In the former case considerable limitations exist, such that it has to be ensured that the compound having an increased biological half time, i.e. retention time in the organism to be treated, does not lose its pharmacological properties, in other words its efficacy as well as causing as little as possible side effects.

Apart from the aptamers mentioned above there exists a further form of functional nucleic acids in the so-called spiegelmers. The spiegelmers too bind specifically to a target sequence, wherein here though it is selected against the enantiomeric form of the target using a D-nucleic acid library, and thereupon the D-nucleic acids binding to it are prepared as L-nucleic acids, and as a result of the chiral reciprocity these are able to bind to the true target and not to the enantiomeric form thereof used for the selection process. Methods for the preparation of such spiegelmers are described, for example, in international patent application WO 98/08856.

Seen purely chemically, spiegelmers are L-nucleic acids, typically L-oligonucleotides, that virtually cannot be degraded by natural enzymes as a result of their assembly from L-nucleotides. Apart from the target specificity, this characteristic qualifies them for use in the most different areas, such as e.g. analysis of biological samples, diagnosis and therapy.

Similar to other chemical compounds, that have applications in diagnostics as well as therapy, particularly those which are applied in an organism, there is thus a need for spiegelmers to convert these into a form, that permits that the spiegelmers are present and effective in an organism over an extended period of time. Thereby it is a further object underlying the present invention, that the target molecule specificity characteristic for the spiegelmers is not influenced by the modification.

According to the invention, the object is solved in a first aspect by a L-nucleic acid comprising a L-nucleic acid part and a non-L-nucleic acid part, and the conjugation of the L-nucleic acid part with the non-L-nucleic acid part leads to a retarded excretion from the organism and renal clearance, respectively, compared to a L-nucleic acid comprising only the L-nucleic acid part.

In a second aspect the object underlying the invention is solved by a modified L-nucleic acid, comprising a L-nucleic acid part and a non-L-nucleic acid part, wherein the conjugation with the non-L-nucleic acid part leads to an increased retention time in an organism compared to a L-nucleic acid comprising only the L-nucleic acid part.

In a third aspect the object underlying the invention is solved by a modified L-nucleic acid, particularly by modified L-nucleic acid according to the invention, comprising a L-nucleic acid part and a non L-nucleic acid part, wherein the non-L-nucleic acid part has a molecular weight of more than about 300 Da, preferably more than about 20,000 Da, and more preferably more than about 40,000 Da.

In one embodiment of the modified L-nucleic acids according to the invention it is intended that the L-nucleic acid part is conjugated with the non-L-nucleic acid part, and that the non-L-nucleic acid part has a molecular weight of more than about 300 Da, preferably more than about 20,000 Da, and more preferably more than about 40,000 Da.

In a further embodiment of the modified L-nucleic acids according to the invention it is intended that the modified L-nucleic acid has a molecular weight of about 600 to 500,000 Da, preferably of about 10,000 to 400,000 Da, more preferably of about 50,000 to 300,000 Da.

In yet a further embodiment of the modified L-nucleic acids according to the invention it is intended that the L-nucleic acid part has a molecular weight of 300 to 50,000 Da, preferably of 5,000 to 25,000 Da, more preferably of 7,000 to 15,000 Da.

Finally in an embodiment of the modified L-nucleic acids according to the invention it is intended that the non-L-nucleic acid part is linked directly or indirectly to the L-nucleic acid part via a functional group of the L-nucleic acid part, which is present on or bound to one of the following components of the L-nucleic acid, wherein the functional group is selected from the group comprising terminal and non-terminal phosphates, terminal and non-terminal sugar portions, and natural and non-natural purine bases and natural and non-natural pyrimidine bases.

In one embodiment of the modified L-nucleic acids according to the invention it is intended that the linkage of the non L-nucleic acid part with the L-nucleic acid part occurs via the 2'-OH—, 3'-OH— and/or 5'-OH— group or a derivative thereof of one or more of the sugar portions of the L-nucleic acid part.

In a further embodiment of the modified L-nucleic acids according to the invention it is intended that the linkage occurs via at least one of the positions 5 or 6 of the pyrimidine base.

In yet a further embodiment of the modified L-nucleic acids according to the invention it is intended that the linkage occurs via at least one of the position 8 of the purine bases.

Finally, in one embodiment of the modified L-nucleic acids according to the invention it is intended that the linkage occurs at one or more of the exocyclic and/or endocyclic amine groups und/or keto groups of the purine and/or pyrimidine bases and/or abasic position(s).

In one embodiment of the modified L-nucleic acids according to the invention it is intended that the non-nucleic acid part is selected from the group comprising linear poly(ethylene) glycol, branched poly(ethylene)glycol, hydroxyethyl starch, peptides, proteins, polysaccharides, sterols, polyoxypropylene, polyoxyamidate, poly(2-hydroxyethyl)-L-glutamine, precise polyethylene glycol.

In one embodiment of the modified L-nucleic acids according to the invention it is intended that a linker is arranged between the L-nucleic acid part and the non-L-nucleic acid part.

In a further embodiment of the modified L-nucleic acids according to the invention it is intended that the L-nucleic acid part comprises a nucleic acid according to SEQ ID NO. 1.

In a preferred embodiment of the modified L-nucleic acids according to the invention it is intended that the L-nucleic acid part has an 6-aminohexylphosphate at the 5'-OH end as a linker.

In particularly preferred embodiment of the modified L-nucleic acids according to the invention it is intended that polyethylene glycol is coupled to the free amine of the aminohexylphosphate linker.

In a fourth aspect the object is solved by using the L-nucleic acids according to the invention as a diagnostic or diagnostic means.

In a fifth aspect the object underlying the invention is solved by the use of the modified L-nucleic acids according to the invention for the preparation of a medicament.

In a sixth aspect the object is solved by a method for the provision of a modified L-nucleic acid, particularly of the nucleic acids according the invention, comprising a L-nucleic acid part and a non-L-nucleic acid part, wherein the following steps are intended:
  a) providing a L-nucleic acid, which forms the L-nucleic acid part or a part thereof of the modified L-nucleic acid;
  b) providing a non-L-nucleic acid, which forms the non-L-nucleic acid part or a part thereof of the modified non-L-nucleic acid;
  c) reacting the L-nucleic acid from a) and the non-L-nucleic acid from b); and
  d) optionally isolating the modified L-nucleic acid obtained in step c).

In one embodiment of the method according to the invention it is intended that the L-nucleic acid in step a) comprises a linker.

In a further embodiment of the method according to the invention it is intended that after providing the L-nucleic acid in step a), it is provided with a linker.

It is furthermore within the scope of the present invention, that the non-L-nucleic acid part comprises a linker and that after providing the non-L-nucleic acid in step b), it is provided with a linker, respectively.

The present invention is based on the surprising finding, that upon the use of L-nucleic acids in an organism as for example an mammalian organism and in particular in a mammal that is selected preferably from the group comprising humans, monkeys, dogs, cats, sheep, goats, rabbits, guinea pigs, mice and rats, though L-nucleic acids are not metabolised, which goes back to the nucleases occurring in such organisms as a rule, do not recognise L-nucleic acids as a substrate due to their stereospecificity, the biological half time of the L-nucleic acids in said organisms is nevertheless comparatively low. So it was noticed, that upon in vivo administration of unmodified L-nucleic acids of a random sequence in rats and monkeys the half time was between 30 minutes and 6 hours. Also, using a L-nucleic acid, i.e. a spiegelmer, that is directed against a target molecule present in the tested organism, the above observation of a comparatively low biological half time was confirmed, which confirms that this is not due to an artefact as a result of the non-specificity of the L-nucleic acid. Furthermore the present inventors noticed, that the half time of non-modified L-nucleic acids is approximately as high as the half time of non-modified D-nucleic acids. At the same time the stability of the non-modified L-nucleic acids clearly increased compared to the stability of non-modified D-nucleic acids. Surprisingly, it could be shown, that because of the modification the half time of L-nucleic acids increases more than upon the modification of D-nucleic acids. Thus, there is going to be a change, completely unexpectedly, in the half time of the modified L-nucleic acids as a result of the modification compared with the half time of the modified D-nucleic acids, whose half times otherwise are similar to each other in the non-modified form. In other words, only as a result of the modification the desired effect of a prolonged half time of functional nucleic acids can be realised, which is possible using modified L-nucleic acids only, and not using modified D-nucleic acids, though. In the specific case described above it is a spiegelmer for the hormone agonist gonadotropin releasing hormone (GnRH), which was administered to male, orchidectomised rats. GnRH stimulates the synthesis and release of the gonadotropins follicle stimulating hormone (FSH) and luteinising hormone (LH) There are increased FSH- and LH levels in male, orchidectomised rats due to the absent testosterone feedback signal. The specific spiegelmer caused a clear lowering of the LH level in a fist study (100 mg/kg, s.c. application), however after a few hours already, a reduction of the efficiency of the spiegelmer could be observed. In a performance of the same study with the corresponding GnRH spiegelmer PEG conjugate (150 mg/kg, i.v. application) a complete lowering of the LH level could be observed, however, which still stayed completely lowered over a period of time of 24 hours. The GnRH spiegelmer PEG conjugate represents an example for a modified L-nucleic acid according to the invention. The GnRH spiegelmer corresponds here to the L-nucleic acid part, and the PEG to the non-L-nucleic acid part.

These results show, that the retention time of L-nucleic acids like spiegelmers in an organism can be extended by a modification, particularly by a high-molecular modification of the L-nucleic acid. The modification of the L-nucleic acid takes place by linking of same with a non-L-nucleic acid. Without intended to be bound by theory, this surprising observation appears to go back to the elimination of the modified L-nucleic acid from an organism, particularly from a mammalian organism is slowed down as a result of the increased molecular weight of a L-nucleic acid modified in such a way. Since the elimination is typically carried out via the kidneys, it is assumed that at present the glomerular filtration rate of the kidneys regarding the modified L-nucleic acids is significantly reduced compared with those of the non-modified L-nucleic acids, which leads to an increased retention time, i.e. biological half time of the modified L-nucleic acid compared to the retention time of the corresponding but not modified L-nucleic acid.

Particularly remarkable in this context is the fact, that despite the modification carried out the modified L-nucleic acid, i.e. in particular the L-nucleic acid part thereof, which is responsible for the target molecule specificity, obviously loses nothing of its specificity. Thus, the modified L-nucleic acids according to the invention completely surprisingly have the characteristics, which otherwise can not normally be realised in other pharmaceutically active compounds, namely that one can do without extensive galenic formulations, for example in form of depot preparations, that release the agent successively, and rather a direct modification of the agent in question can be brought about, without its biological activity being negatively influenced, in case of the spiegelmers particularly expressed as specificity of the reaction or the formation of a complex with their respective target molecule. In other words, the modified L-nucleic acids according to the invention overcome the incompatibility of the pharmaceutically active agent with an increase of its retention time in an organism, in particular with a reduction in elimination as for example in glomerular filtration rate that exists otherwise in pharmaceutically active agents and particularly in small agent molecules of specific activity. Here, it is remarkable that the affinity of the L-nucleic acid part remains essentially unchanged by the conjugation with the non-L-nucleic acid part.

The previously said applies of course not only in case of the use of modified L-nucleic acids like spiegelmers as therapeutically active agents, but also for their use as diagnostic means, particularly to their use as in vivo diagnostics. A typical example of the use of spiegelmers as in vivo diagnostics is the in vivo imaging, and herein the use of radionucleotide carrying spiegelmers for the positron emission tomography, in particular. In this application, it is geared towards the radionucleotide surviving for an exactly defined period of time. Would the radionucleotide and thus the radioactivity stay within the organism for a longer period of time, wherein longer is meant to be taken as necessary to carry out the respective examination, this would be accompanied by an exposition to radioactive radiation unnecessary for the patient and in some cases possibly even posing a health risk. On the other hand, in the case that die elimination of the diagnostic means and thus the radioactive label from the body occurs too fast, this would lead to no appropriate diagnosis or diagnostic statement being possible. With the availability of the modified L-nucleic acids according to the invention the diagnostic means can be adjusted in an optimised manner depending on the respective requirements with regard to its retention time, i.e. its biological half time. This is largely based too on the observation, that the glomerular filtration rate becomes severely limited from a molecular weight of more than about 45,000 Da onwards. Otherwise the elimination, in particular the glomerular filtration rate, is clearly correlated with the size of the molecule. By using a suitable non-L-nucleic acid part, as for example those described herein, the retention time of the modified L-nucleic acid can be adjusted exactly to the requirements.

The chemical nature of the non-L-nucleic acid part of the modified L-nucleic acid can be designed virtually freely within the scope of certain limits. A requirement for the modified nucleic acid administered into an organism, which should be fulfilled in the multitude of cases of application of the modified L-nucleic acid, is that the non-L-nucleic acid part consists of one or more non-immunogenic compounds. Alternatively, but if applicable also additionally thereto, these may be lipophile compounds as well as hydrophile compounds. For the person skilled in the art it is obvious, that depending on the general conditions of the isolated case also slightly immunogenic compounds may be recruited, in particular if the administration of the modified L-nucleic acid according to the invention is not intended to occur over a longer period of time or repeatedly, but merely one time. In turn, this aspect is particularly of importance, if the modified L-nucleic acids according to the invention have to be administered over a longer period of time or repeatedly. As a rule, it will have to be ensured, that no immune response is generated by the non-L-nucleic acid part of the modified L-nucleic acid according to the invention upon application of the modified L-nucleic acid, which upon renewed administration of the same, would lead to an immunologic or allergic reaction.

The non-L-nucleic acid part of the modified L-nucleic acid may be designed such that more than one non-L-nucleic acid part is bound to or conjugated with a L-nucleic acid part. For example, it is possible, that two or more non-L-nucleic acid parts are bound to the L-nucleic acid part. The single non-L-nucleic acid part is preferably a polymer, wherein the subunits of the polymer may have a comparatively low molecular weight. It is also within the scope of the present invention, that more than one L-nucleic acid part is bound to a non-L-nucleic acid part.

A further aspect, that has to be taken into consideration when selecting the non-L-nucleic acid part of the modified L-nucleic acid, is the addressing of the spiegelmers to certain compounds, particularly to certain organs or cells. Here, depending on the specific circumstances, the non-L-nucleic acid part can be adjusted such that the modified L-nucleic acid accumulates preferably in certain cells, tissues or organs, independent of the binding specificity of the spiegelmer or the modified L-nucleic acid, caused by the L-nucleic acid part.

Typically, the molecular weight of the non-L-nucleic acid part is between 300 and 500,000 Da. The L-nucleic acid part can be coupled either individually, multiply, or in any combination with other non-L-nucleic acid parts onto same or different locations of the L-nucleic acid part of the modified L-nucleic acid.

It is within the scope of the present invention, that the molecular weight of the modified L-nucleic acid is strongly determined by the non-L-nucleic acid part. Basically, the modified L-nucleic acid may have a molecular weight from around 600 to 500,000 Da, preferably from around 10,000 to 400,000 Da and more preferably from around 50,000 to 300,000 Da. Lower molecular weights are realised for example by modified L-nucleic acids of a kind, that are cholesterol conjugates and typically have a molecular weight from around 10 kDa to 25 kDa. Higher molecular weight ranges are realised for example by modified L-nucleic acids of a kind, that are HES conjugates and often have a molecular weight from around 100 kDa to 500 kDa. In the case, that the modified L-nucleic acids are PEG conjugates, the preferred molecular weight is around 40 to 70 kDa.

As a non-L-nucleic acid part can be used for example:

polyether, alkoxypolyether, as for example linear or branched poly(ethylene)glycols (PEG), methoxypoly(ethylene)glycols, ethoxypoly(ethylene)glycols, precise PEG (wherein precise PEG is a polyamide of the form (—NH—Y—NH—CO—X—CO—), wherein Y and Z may be varied at each location as (—$CH_2CH_2O$—)$_p$ with different p in the range of 4-6), poly(2-hydroxyethyl)-L-glutamines, polyoxypropylenes, which are distinguished in particular by not being metabolisable in vivo and inasmuch the effect of the controlled elimination caused by the size, i.e. the molecular weight of the modified L-nucleic acid is particularly lastingly reflected and is not interfered by breakdown processes in the non-L-nucleic acid part.

peptides, polypeptides and proteins, such as e.g. albumin, wherein these compounds may be naturally existing ones as well as substances added from the outside.

polysaccharides, as e.g. hydroxyethyl starch, dextranes, are as far as they are concerned metabolisable and are able to influence the retention time very specifically, as a result of the exactly controllable degradation rate. The molecular weight of the hydroxyethyl starch, used in one embodiment is between 10 kDa, preferably between 40 kDa and 400 kDa, preferably between 100 kDa and 300 kDa. Hydroxyethyl starch has a molar degree of substitution from 0.1 to 0.8 and a ratio of $C_2$:$C_6$ in the range of 2 to 20. Regarding the coupling of the polysaccharides onto the L-nucleic acid part of the modified L-nucleic acid applies what was said herein in the context of the sugar portion of the L-nucleic acids regarding the use of the OH groups and their derivatisation.

sterols, as e.g. cholesterol. Though sterols are distinguished by a relatively low molecular weight, however, this already may lead to an increase in the retention time of the L-nucleic acid modified in such a way. Of more importance still in this respect is the behaviour of the sterols to be judged, in particular of cholesterol, which forms a non-covalent complex with lipoproteins in vivo, such as for example HDL, whereby an enlargement of the molecule and thus a longer half time is achieved.

Basically, it is within the scope of the present invention, that the non-L-nucleic acid part is formed too from one or more D-nucleosides and D-nucleotides, respectively, wherein these may have further modifications, individually or as a whole, as for example modifications for increased stability in biological systems. Such modifications are for example the fluoridation at the position 2' of the sugar portion of the nucleotides and nucleosides, respectively. Furthermore, these D-nucleosides and D-nucleotides may be a component of the different non-L-nucleic acids, particularly of those previously mentioned, but also a part of one of the linkers described herein. Here, it is within the scope of the present invention, that individual or several of the D-nucleosides or D-nucleotides may comprise also one or more abasic positions.

The linkage of the L-nucleic acid part with one or more of the non-L-nucleic acid parts may occur on principle at all components or groupings of the two parts assembling the modified L-nucleic acid, wherein it may be intended that derivatisations occur at one or more locations of one or both parts, i.e. at the L-nucleic acid as well as at the non-L-nucleic acid part(s). The linkage may occur in particular at the 5'-OH, 3'-OH or the 2'-OH group of the L-nucleic acid, in particular at the ribose or deoxyribose part thereof.

At the same time it is also within the scope of the present invention, that at least a portion of the sugar components of the nucleotides assembling the L-nucleic acid may have a sugar other than ribose or deoxyribose. Such sugars may be for example further pentoses, such as for instance arabinose, but also hexoses or tetroses or may contain also a nitrogen atom, as for example in a morpholino ring or aza- or thio sugar, or further sugar modifications as in locked nucleic acids (LNA) or peptide nucleic acids (PNA). These OH groups may by appropriate chemical modification be present as $NH_2$, SH, aldehyde, carboxylic acid, phosphate, iodine, bromine, or chlorine groups. Further functional groups, which allow a linkage onto the L-nucleic acid part, are known to the person skilled in the art. As far as the linkage of non-L-nucleic acid part with a L-nucleic acid part is described herein, the comments apply basically also for the case that more than one non-L-nucleic acid part is linked to the L-nucleic acid part or bound to it, provided that no statements to the contrary are given.

It is further within the scope of the present invention that at least one part of the phosphate groups of the nucleotides assembling the modified L-nucleic acid has modification. Such modifications are for example phosphothioates, phosphodithioates, phosphoamidates, phosphonates and further modification known to persons skilled in the art.

Apart from the linkage of the L-nucleic acid part to the non-L-nucleic acid part via the sugar portion of the L-nucleic acid part, the linkage may occur also at the phosphate backbone, wherein here too, as pointed out in the context of the linkage via the ribose or deoxyribose part of the L-nucleic acid, a corresponding modification may occur. Eventually, linkages via the position 5 and/or 6 of the pyrimidine base(s), position 8 of the purine base(s), as well as the exo- and endocyclical amine and keto groups of the respective nucleobases are possible, if applicable also after functional modification of the same, as elaborated on above. Apart from natural bases the L-nucleic acid may contain one or more non-natural bases, like e.g. isoguanidine, isocytidine, xanthosine, inosine, 2,4-diaminopyrimidine. Here it is within the scope of the present invention that any of the linkages described herein between the L-nucleic acid part and the non-L-nucleic acid part may occur directly or indirectly. An indirect linkage is present in particular if a linker is arranged between the L-nucleic acid part and the non-L-nucleic acid part, for example a linker described herein, and provides one or both of the functional groups.

It is also within the scope of the present invention that between the L-nucleic acid part and the non-L-nucleic acid part(s) one or more so-called linker may be included. Such a linker typically consists of at least one functional group as well as a means for distance keeping or a spacer. On one hand, the function of this linker may consist in facilitating the coupling reaction. In addition or alternatively it may impart a function such that a spatial distance is built up between the L-nucleic acid part and the non-L-nucleic acid part of the modified L-nucleic acid. Such a distance is of advantage under certain circumstances, for instance if interactions between the parts assembling the modified L-nucleic acid, in particular between the L-nucleic acid part and the non-L-nucleic acid part or between two or more non-L-nucleic acid parts of the modified L-nucleic acid are to be prevented.

In turn, the linker itself may comprise one or more functional groups and be linked at one of the sites of the L-nucleic acid part mentioned above to the latter. Typically the spacer consists of i.a. alkyl chains of different length, wherein a chain length of 1 to 20, in particular of 4 to 15 und further in particular 6 to 12 C-atoms is preferred. The alkyl chain itself may be branched or carry further functional groups. A typical embodiment of the spacer comprises ether linkages between single monomers, such as are present in e.g. poly(ethylen) glycol or polyproxylene, wherein here the monomers are often present 1 to 20 times in the polymers. Also, in forming the spacer from polyaminealkyl or polyamidoalkyl chains a frequency of a value of 1 to 20 is common for monomers assembling these polymers.

The linker may either be coupled to one of the L-nucleotides, that form the L-nucleic acid part of the modified L-nucleic acid. Alternatively, the linker may be included into the emerging oligomer during the enzymatic or chemical synthesis of the L-nucleic acid. Furthermore, it is within the scope of the present invention that the L-nucleic acid is modified post synthetically und is thereby provided with a linker for the coupling of a non-L-nucleic acid part.

It is also within the scope of the present invention that a linker is included for example, in an abasic position in a hairpin loop or a the 3'- or 5'-end or at another position.

If the L-nucleic acid is a spiegelmer the abasic position may be included at a position of the spiegelmer, that is not essential for binding of the target molecule, and for the structure of the spiegelmer, respectively. Abasic position refers here to a site of the L-nucleic acid part, that analogously to a normal nucleotide possesses the same backbone from phosphate and sugar, but in which the nucleobase is substituted by a hydrogen atom or a linker, as is also shown in FIG. 24.

The modified L-nucleic acids, herein referred to also as L-nucleic acid conjugates, as already evident from the itemisation above regarding the linkage sites between the L-nucleic acid part and the non-L-nucleic acid part may be prepared by a number of reactions, as elaborated on in more detail in the following.

Acid amides may be prepared by reaction of N-hydroxysuccinimid (NHS) or similar activations of carbonic acids, such as anhydride, acid chloride, esther, succinimid and maleimide from a primary or secondary amine[1,2].

Thioether may be prepared starting from a halide or thiol[3,4] and may subsequently be subject of an oxidation into sulphoxide or sulphone[5,6] Halides, in particular haloacetyl (iodoacetic acid, bromoacetic acid) may be coupled to any functional group of one of both L-nucleic acid parts per ester or acidamide bond, and subsequently the highly reactive iodine or bromine group may be coupled with a free thiol. Haloacetyl is therfore a special case of the halogenide thiol coupling[7]. Thioether may also be prepared starting from maleimide and thiol[7-9], isothiourea from isothiocyanate and amine[10], isourea starting from isocyanate and amine[11], carbamate starting from isocyanate and alcohol[12], C—C linkages by means of a Diels-Alder reaction[13], heterocycles by 1,3dipolar cycloaddition[13], amines by reductive amination, following the reaction of; for instance, aldehyde or ketone with an amine upon subsequent reduction[14], acidamide starting from an acid and an amine[15,16], ester starting from carbonic acid or the activated carbonic acids mentioned above and alcohol, sulphonamide starting from amine and sulphonylchloride[17], secondary amines starting from an epoxide and an amine[18,19], thioether starting from an epoxide and a thiol[20], a disulphide starting from a thiol and a further thiol or a disulphide[21,22], hydrazones starting from a hydrazine and an aldehyde or a ketone, wherein the hydrazone may be further reduced to a stable modified hydrazine[23], phosphothiates starting from a phosphate or an activated phosphoric acid, such as for example phosporoimidazolide and a thiol[24], phophoramidate starting from a phosphate or an activated phosphoric acid, such as for example phosporoimidazolide or phos-N-hydroxyd benzotriazole and an amine[24-27]. Thereby, it is within the scope of the present invention to couple first a linker via a phosphoamidate or phosphothioate linkage to the L-nucleic acid part and subsequently to the non-L-nucleic acid part. Such linkers may be ethylendiamine or cysteamine, in particular.

In principle, the explanations above apply also to the case, that the reactive starting group first mentioned is arranged at the non-L-nucleic acid part as well as to case that is arranged at the L-nucleic acid part. The corresponding modification of the L-nucleic acid in the sense that a corresponding reactive group is provided, is known to the persons skilled in this art. The same applies to the non-L-nucleic acid part.

The term L-nucleic acid is used herein synonymously to the term L-oligonucleotide or L-polynucleotide and refers, amongst others, L-deoxyribonucleic acid as well as L-ribonucleicacid and combinations thereof, i.e. that single or a group of nucleotides are present as RNA and the further nucleotides making up the nucleic acid are present as DNA or vice versa. Here, it is also intended that instead of deoxyribose or ribose other sugars may form the sugar component of the nucleotide. Furthermore, the use of nucleotides with further modifications at position 2', is comprised, such as $NH_2$, OMe, OEt, OAlkyl, NHAlkyl and the use of natural and non-natural nucleobases, as for example isocytidine, isoguanosine. It is thereby also within the scope of the present invention that the L-nucleic acid has so-called abasic positions, i.e. nucleotides, whose nucleobase is absent. Such abasic positions may be arranged within the nucleotide sequence of the L-nucleic acid as well as at one or both of the ends, i.e. the 5'- and/or the 3'-end.

It is further within the scope of the present invention that the L-nucleic acid contains one or more D-nucleosides or D-nucleotides. Here, the one or the several D-nucleosides or nucleotides may be arranged within the L-nucleic acid as well as at one or both of the ends of the L-nucleic acid. The single D-nucleoside or D-nucleotide may carry one or more modifications, for example for increasing the stability of the nucleoside or the nucleotide, respectively, and its binding to the L-nucleic acid, respectively.

In principle, the L-nucleic acid may be present double or single strandedly. Typically, it is a single stranded L-nucleic acid, which may, however, form defined secondary structures and thus tertiary structures also, due to its primary sequence. In the secondary structure a multitude of L-nucleic acids has double stranded sections.

Apart from the high molecular modifications described herein in particular, L-nucleic acids may also refer to modifications with regard to single nucleotides of the nucleic acid, wherein here e.g. the 2'-OH group of the sugar portion of the nucleotides may be present as a methylether, as already disclosed above.

The L-nucleic acids and L-nucleic acid parts, respectively, described herein are preferably functional nucleic acids. To the functional nucleic acids belong, amongst others, aptamers, spiegelmers, ribozymes and aptazymes. Preferably, the L-nucleic acids and L-nucleic acid parts, respectively, are spiegelmers. As mentioned already in the beginning, spiegelmers are nucleic acids that bind to a target molecule or a part thereof and are made up from L-nucleotides, at least in the part of the nucleic acid binding to the target molecule. Preferably, they are the result of contacting a nucleic acid library, in particular a statistical nucleic acid library, with the target molecule.

For a selection method for the development of functional nucleic acids combinatorial DNA libraries are prepared first. As a rule, it is a synthesis of DNA oligonucleotides, that contain a region from 10-100 randomised nucleotides in the center, which is flanked 5'-und 3'-terminally by two primer binding sites. The preparation of such combinatorial libraries is described, for example, in Conrad, R. C., Giver, L., Tian, Y. and Ellington, A. D., 1996, Methods Enzymol., Vol 267, 336-367. Such a chemically synthesised single stranded DNA library can be converted into a double stranded library by the polymerase chain reaction, which may be used for a selection by itself. As a rule, a separation of the individual strands takes place with suitable methods, such that a single stranded library is regained, which is used for the selection method, if it is a DNA selection (Bock, L. C., Griffin, L. C., Latham, J. A., Vermaas, E. H. und Toole, J. J., 1992, Nature, Vol. 355, 564-566). It is still just as possible to use the chemically synthesised DNA library directly for the in vitro selection. In addition, an RNA library may, in principle, be generated from double stranded DNA, if a T7 promoter has been included previously, also by a suitable DNA dependant polymerase, e.g. T7 RNA polymerase. Aided by the methods described, it is possible to generate libraries of $10^{15}$ and more DNA or RNA molecules. Every molecule from this library has a different sequence and thus a different three-dimensional structure. By the in vitro selection methods it is now possible to isolate one or more DNA molecules from the mentioned library, that have a significant binding property towards a given target, by one or more cycles of selection and amplification as well as mutation, if applicable. The targets may be viruses, proteins, peptides, nucleic acids, small molecules such as metabolites of the metabolism, pharmaceutical agents and metabolites thereof, or other chemical, biochemical or biological compounds, such as described, for example, in Gold, L., Polisky, B., Uhlenbeck, O. und Yarus, 1995, Annu. Rev. Biochem. Vol. 6, 763-797 and Lorsch, J. R. and Szostak, J. W., 1996, Combinatorial Libraries, Synthesis, Screening and application potential, ed. Riccardo Cortese, Walter de Gruyter, Berlin. The prodcedure is performed in such a manner, that binding DNA or RNA molecules are isolated from the library initially used, and are amplified after the selection step by means of polymerase chain reaction. In RNA selection a reverse transcription is to be placed ahead of the amplification step by polymerase chain reaction. A library enriched after a first round of selection may be used for a renewed round of selection, such that the molecules enriched in the first round of selection have a chance to prevail again by selection and amplification and go into a further round of selection with even more daughter molecules. At the same time the step of the polymerase chain reaction presents the possibility to introduce new mutations during amplification, e.g. by varying the salt concentration. After sufficient rounds of amplification and selection the binding molecules prevailed. An enriched pool emerged this way, whose members may be separated by cloning, and subsequently determined with regard to their primary structure by common methods for determining a sequence. The obtained sequences are then tested for their binding properties with regard to the target. The method for the generation of such aptamers is also referred to as SELEX method and described, for example, in EP 0 533 838, the disclosure of which is hereby included by reference.

The best binding molecules may be shortened to their essential binding domain by shortening of the primary sequences, and prepared by chemical or enzymatical synthesis.

A special form of aptamers manufacturable in such a manner are the so-called spiegelmers, which are characterised essentially by being assembled at least partially, preferably completely, from the non-natural L-nucleotides. Methods for the preparation of such spiegelmers are described in PCT/EP 97/04726, whose disclosure is included hereby by reference. The specific feature of the method described therein, is the generation of enantiomeric nucleic acid molecules, i.e. of L-nucleic acid molecules, that binds to a native target, i.e. being in its natural form or configuration, or such a target structure. The in vitro selection method described above is used to select binding nucleic acids or sequences initially against the enantiomers, i.e. the non-natural structure of a natural target, as for instance in case that the target molecule is a protein, against a D-protein. The resulting binding molecules obtained this way (D-DNA, D-RNA, and corresponding D-derivatives, respectively) are determined as to their sequences and the identical sequence is then synthesised with mirror-image nucleic acid modules (L-nucleotides and L-nucleotide derivatives, respectively). The resulting mirror-imaged enantiomeric nucleic acids (L-DNA, L-RNA, and corresponding L-derivatives, respectively), so-called spiegelmers, have for reasons of symmetry a mirror-imaged tertiary structure and thus a binding property for the target present in its natural form or configuration.

The target molecules described above, also referred to as target, may be molecules or structures, such as e.g. viruses, viroids, bacteria, cell surfaces, cell organelles, proteins, peptides, nucleic acids, small molecules such as metabolites of the metabolism, pharmaceutical agents and metabolites thereof, or other chemical, biochemical or biological compounds.

In the following, the invention is illustrated further by the figures and examples from which further advantages, embodiments and features of the invention ensue.

FIG. 1 shows an hexylamine linker, that has a linear spacer ("means for distance keeping") consisting of six carbon atoms as well as a terminal amino group and a terminal phosphate residue. The substitution denoted with R may present here also a nucleic acid, and the L-nucleic acid part of a modified L-nucleic acid, respectively. Via the amino group the non-L-nucleic acid part may be coupled onto the L-nucleic acid part and thus the modified L-nucleic acid according to the invention be formed.

FIG. 2 shows further linkers, wherein the structures referred to as (2), (4), and (6) correspond to linker according to (1), (3) and (5), wherein in the latter the phosphate part provided with residue R represents preferably the L-nucleic acid part, and the non-L-nucleic acid part of the modified L-nucleic acid is coupled via the functional group called X onto the L-nucleic acid. The term "oligo" stands exemplaryly for an oligonucleotide, wherein it is within the scope of the present invention, that this and the L-nucleic acid or the L-nucleic acid parts, respectively, herein may be generally L-polynucleotides. The various substituents refer herein to the following reactive groups, that are individual and each independent from each other:

X=OH, $NH_2$, HS, Hal, CHO, COOH

Y=O, NH, NMe, S, $CH_2$ $Z_1$, $Z_2$, $Z_3$, $Z_4$, $Z_5$ and $Z_6$=H, Me, Alkyl, $HO(CH_2)_n$, HO, $H_2N(CH_2)_n$, $H_2N$, F, wherein n is an integer between 1 and 20 and wherein Alkyl refers to linear and branched hydrocarbon chains with preferably 1-20 C-atoms, more preferably 1 to 4 C-atoms and/or —$(CH_2)_n$H, —$CH[(CH_2)_nH][(CH_2)_mH]$, —$C[(CH_2)_nH][(CH_2)_mH][(CH_2)_1H]$, —$(CH_2)_n(CH)_m[(CH_2)_1H][(CH_2)_kH]$, —$(CH_2)_n(C)_m[(CH_2)_1H][(CH_2)_kH][(CH_2)_jH]$, wherein n, m, 1, k und j are integers independent from each other between 1 and 8, preferably 1 to 4 C-atoms.

FIG. 3 shows an overview of different linkers, that are coupled to different positions of the nucleobases. Thereby, it is notable that the sugar portion of the nucleoside shown in each case may be a ribose, a deoxyribose or a modified ribose and modified deoxyribose, respectively, and the residue X may be=H, HO, $H_2N$, MeO, EtOH or alkoxy. Thereby, alkoxy, in particular, refers to linear and branched oxyhydrocarbon chains with 1-20 C-atoms, preferably 1 to 4 C-atoms and/or —$O(CH_2)_nH$, —$CH[(CH_2)_nH][(CH_2)_mH]$, —$OC[(CH_2)_nH][(CH_2)_mH][(CH_2)_1H]$, —$O(CH_2)_n(CH)_m[(CH_2)_1H][(CH_2)_kH]$, —$(CH_2)_n(C)_m[(CH_2)_1H][(CH_2)_kH][(CH_2)_jH]$, wherein n, m, 1, k und j are integers independent from each other between 1 and 8, preferably 1 to 4 C-atoms. The actual linker structure is $X_1$-$[X]_n$ in all four nucleosides (1), (2), (3) and (4) shown, wherein n is an integer between 0 and 20. $X_1$ represents a functional group that is selected from the group comprising HO, $H_2N$, HRN, HS, SSR, Hal, CHO, COOH, COOR and COHal. In the linkers denoted as structural formulas (5-12) n is an integer between 0 and 20 as well, and Z means independently from other sustituents either O, NH, NR or S, wherein R stands for alkyl as defined herein.

FIG. 4 shows possible linkers at position 5 of pyrimidine nucleosides and nucleotides, respectively. With regards to residues R', R'' and R''' basically applies what was said herein in the context of FIG. 5. The linker R has the structure —$[Y]_n$—$X_1$ and may preferably acquire the forms shown in structures (2) to (9), wherein Z may mean O, NH, NHR or S here too, independently of the choice of the other substituents, and n may be an integer between 1 and 20. The functional group $X_1$ is preferably selected from the group that has HO, $H_2N$, HRN, HS, SSR, Hal, CHO, COOH, COOR, COHal.

FIG. 5 shows in 1 the basic structure of cytosine, which may have different linker structures at its exocyclic amine. Thereby R' refers to a L-nucleic acid or a L-polynucleotide, OH, or phosphate, R'' to a L-nucleic acid or a L-polynucleotide, OH or phosphate and R''' to H, OH, OMe, OEt, $NH_2$.

The residue R refers thereby to the linker, which has the basic structure $—[Y]_n—X_1$ and may have the structural formulas shown in (2) to (9), wherein Z=O, NH, NR, S and n may be an integer between 1 and 20. The functional group $X_1$ is preferably selected from the group that has HO, $H_2N$, HRN, HS, SSR, Hal, CHO, COOH, COOR, COHal.

FIG. 6 shows the formation of a modified L-nucleic acid according to the invention by reaction of PEG-NHS with a L-nucleic acid provided with a linker. After successful coupling the modified L-nucleic acid is present, that comprises in the present case PEG as the non-L-nucleic acid part and in this actual case an oligonucleotide as L-nucleic acid, wherein a linker or a spacer, respectively, carrying an amino group is inserted between both, and it comes to an acid amid binding between the linker and the PEG. Apart from the modified L-nucleic acid the N-hydroxysuccinimide split off the PEG is obtained as a further reaction product. As possible residues R, H, $CH_3$ and in general alkyl chains with a length of 1-20 are preferred. The functional group may in principle be the product of any one of the reactions explained herein above. Insofar, the embodiments of the linker described in association with the further figures, in particular FIGS. 2 and 3, apply also to this context. The same applies to the substituents and control variables like n depicted in the formula.

FIG. 7 shows the conversion of different PEG derivatives with different linkers. Here, the two reactions (1) and (2) differ only in that in reaction (1) the carboxyl group is present at the PEG and in reaction (2) the carboxyl group is present at a L-oligonucleotide provided with a linker. The functional group of the respective corresponding reaction partner, i.e. in the case of reaction (1) the L-nucleic acid provided with a linker, and in the case of reaction (2) the PEG provided with an amine group. Thus the statement is confirmed, that was made in the context of the different reactions as above, which are possible between a L-nucleic acid part and a non-L-nucleic acid part, if applicable with participation of one or more inserted linkers, that in principle the mentioned reactive groups may be present in all reaction partners that are involved. The finally obtained structures will differ from each other correspondingly, so that in case of reaction (1), where an acid amide group is present at the PEG, and in the case of reaction (2), where the acid amide binding is present at the construct from linker and oligonuleotide, i.e. the L-nucleic acid. With regard to the substituents R applies what was said in the context of FIG. 6, correspondingly.

FIG. 8 shows the reaction of a halogenide with a thioester, that are attached either to the non-L-nucleic acid part or to the L-nucleic acid part, respectively. In the reactions (1) to (3) it is intended that the L-nucleic acid, here as in all figures abbreviated as oligo, is provided with a linker, and that the linker carries a halogenide, as for example I, Br, Cl. This derivatised L-nucleic acid is thereupon reacted with a PEG provided with a thiol group, preferably a terminal thiol group. In the case of reaction (1) a thioether bond between linker and PEG will occur. By oxidation it may result, as depicted in reaction (2), in the formation of a sulphoxide or a sulphone, respectively. In the reactions according to (4) to (6) also a reaction between a thiol and a halogenide occurs, wherein in these cases the L-nucleic acid is provided with the thiol group, and the linker carries the halogenide. Correspondingly, a formation of compounds occurs, wherein the sulphur is arranged between the L-nucleic acid and the linker, and it may be oxidised, as shown in the reactions (5) and (6), again into the corresponding derivatives.

Figure 1:
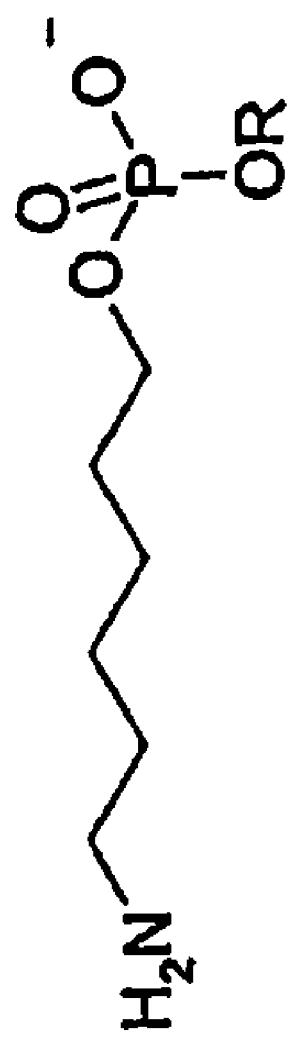
Figure 2:
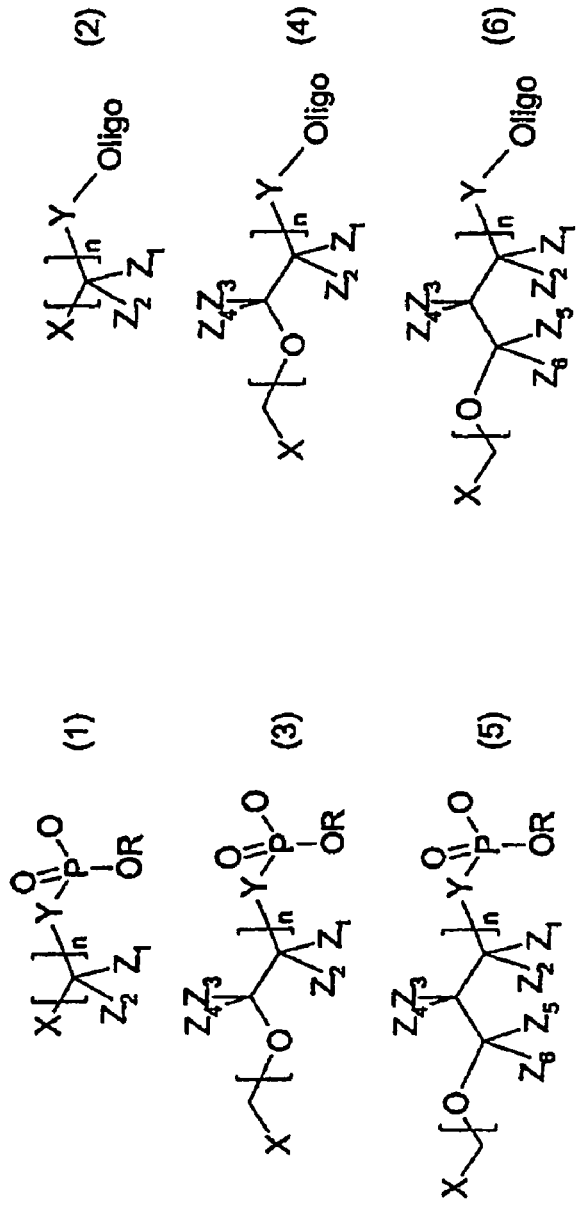
Figure 3:
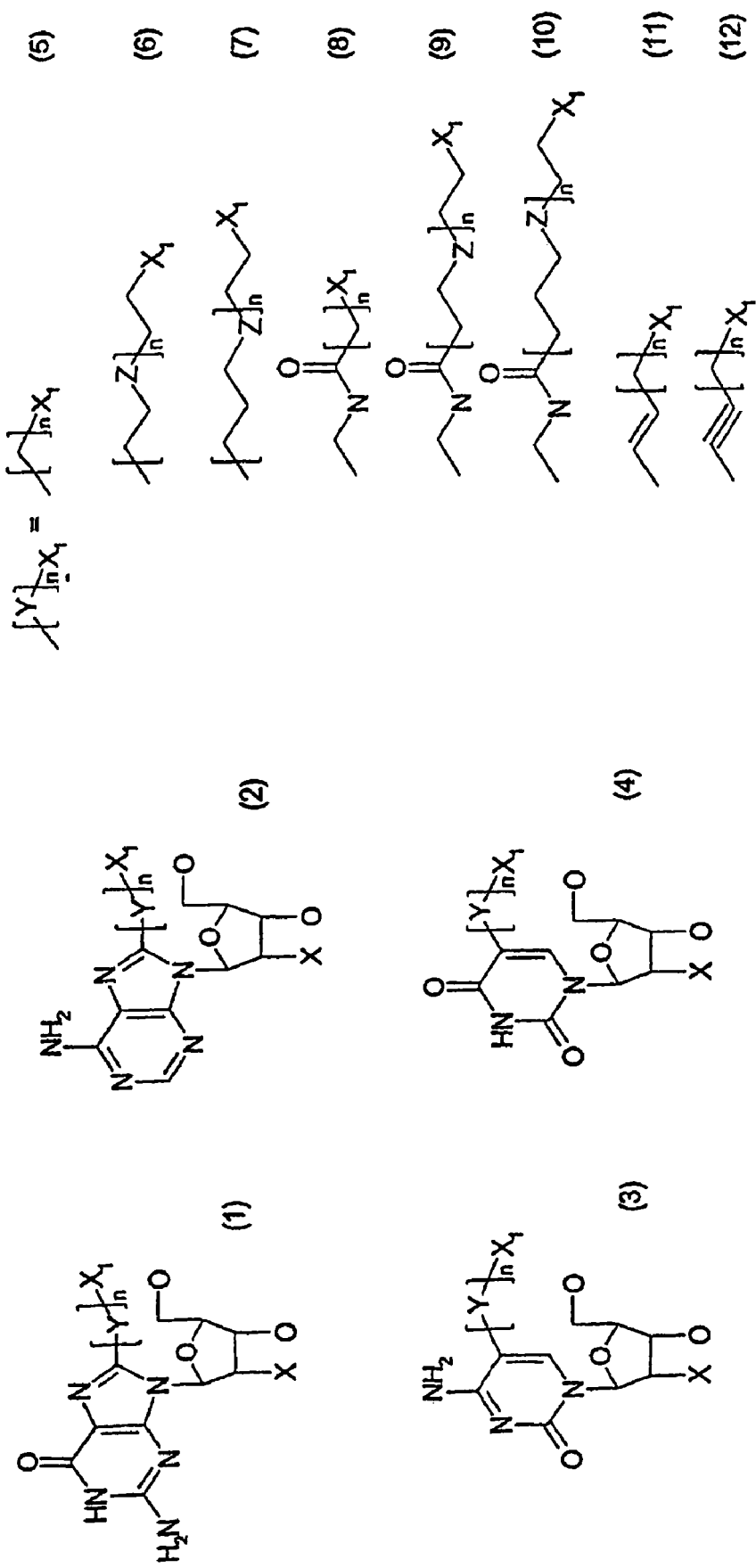
Figure 4:
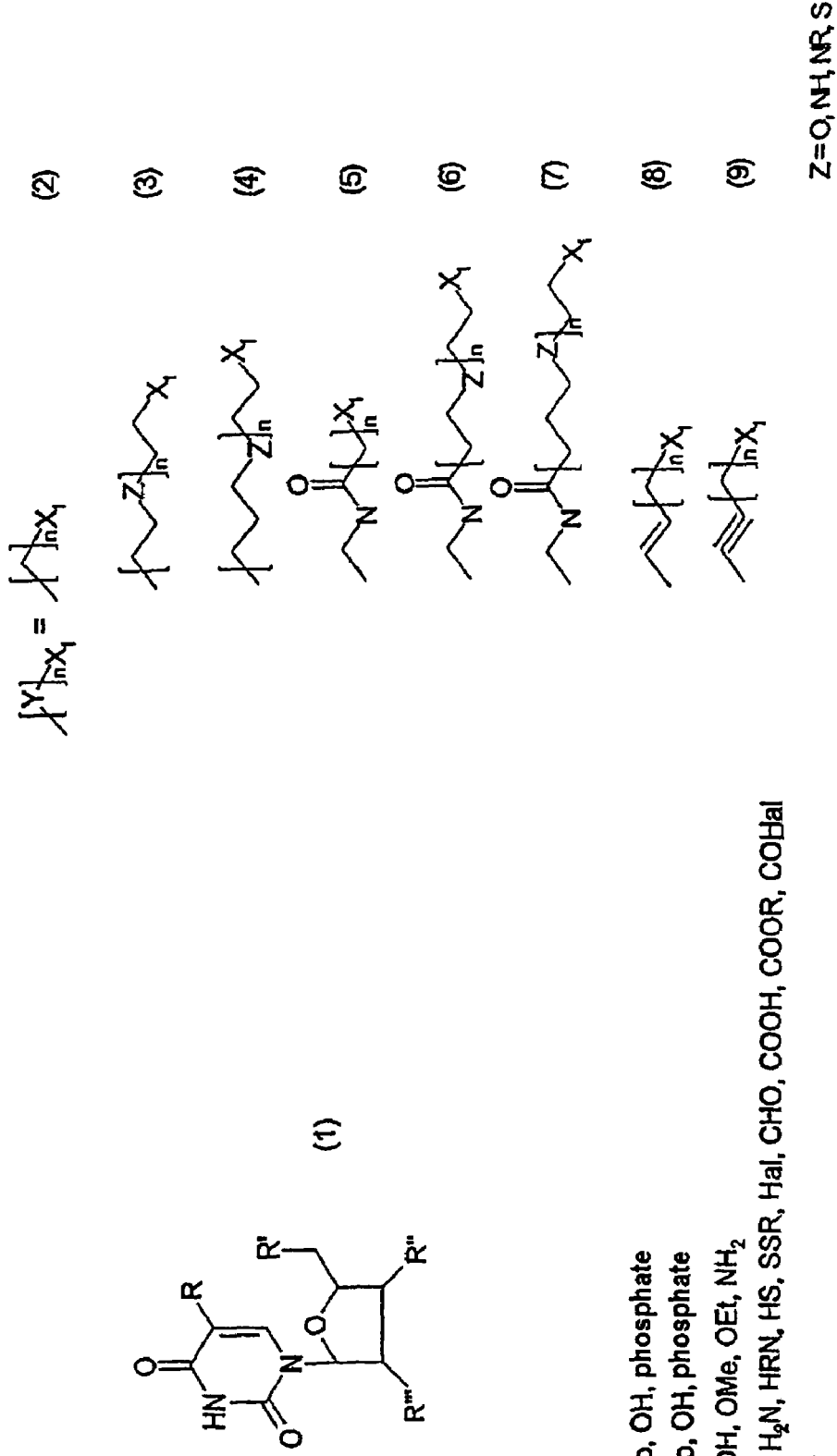
Figure 5:
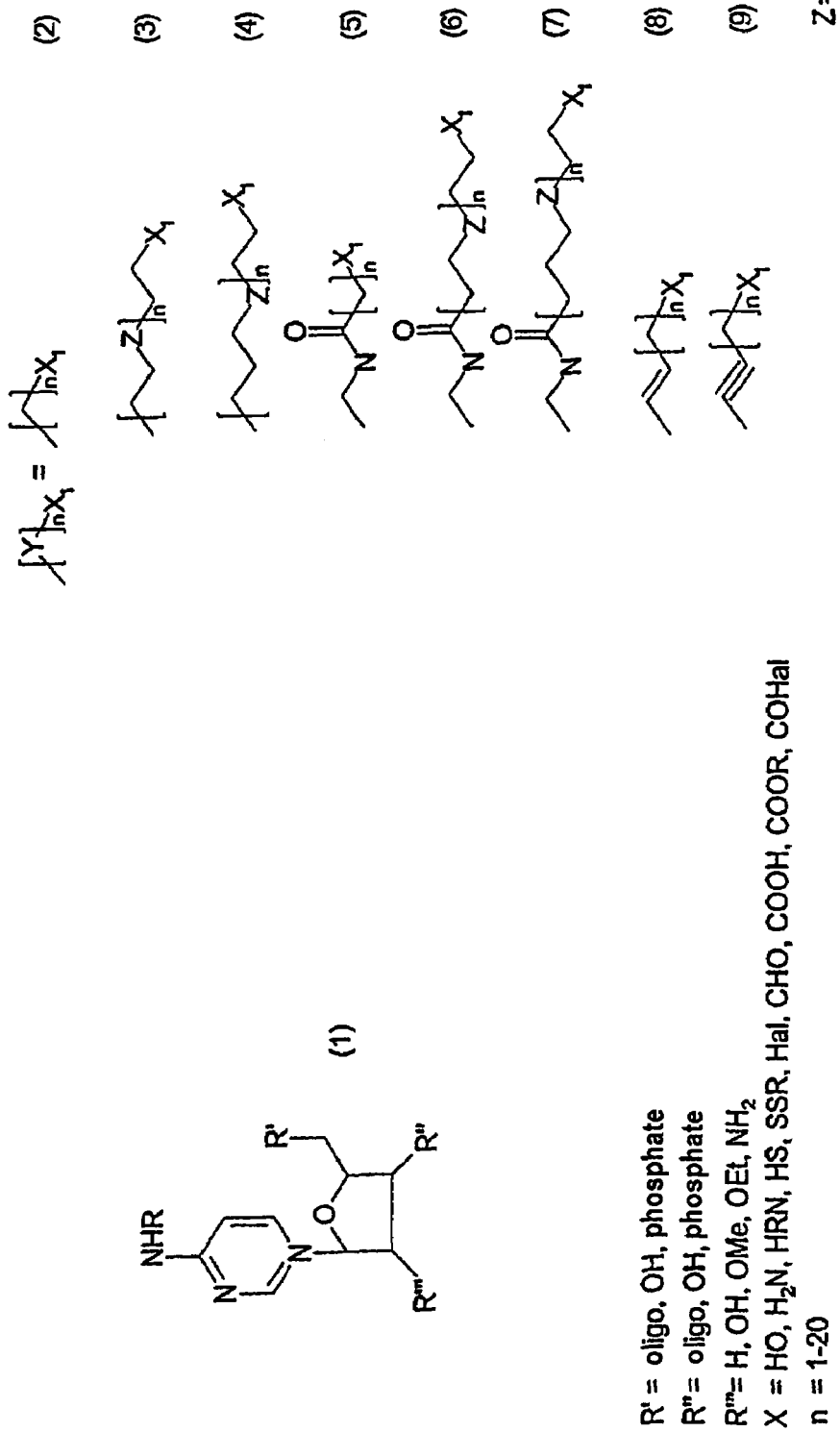
Figure 6:
Figure 7:
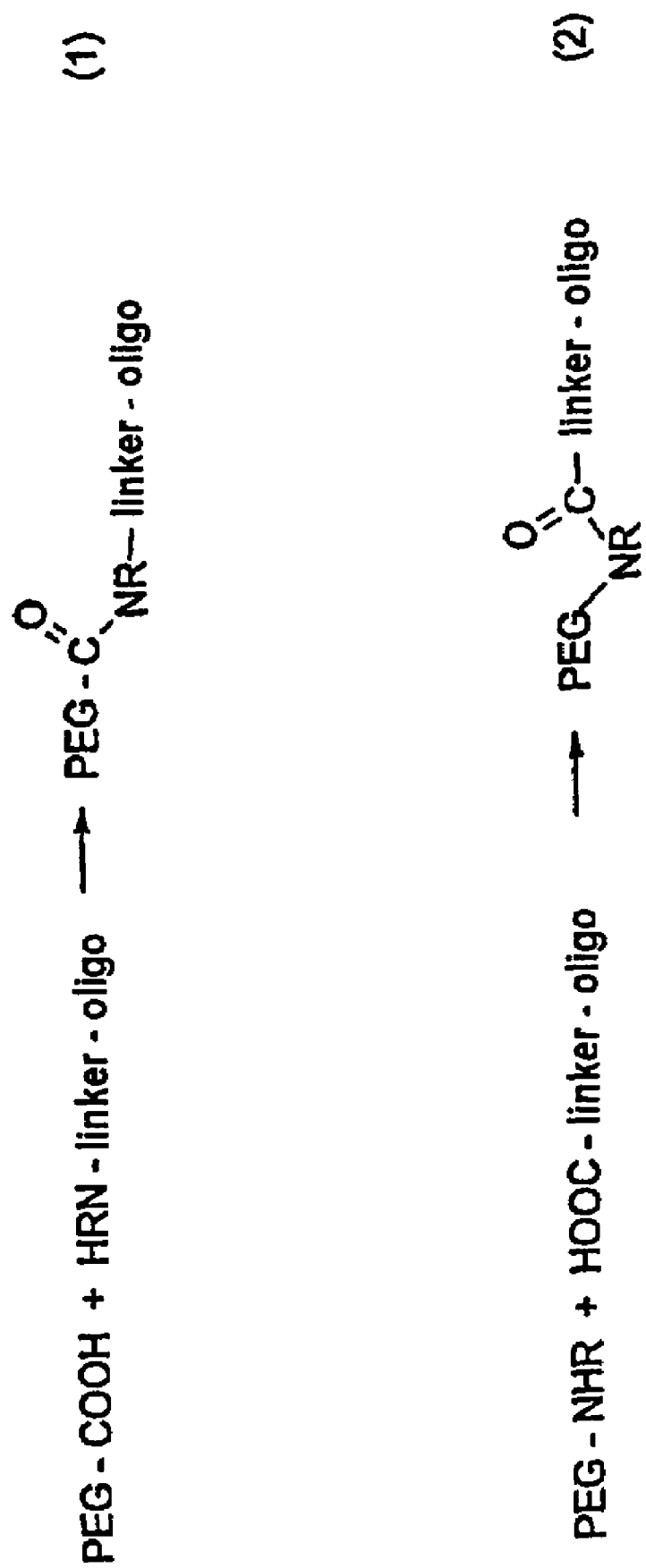
Figure 8:
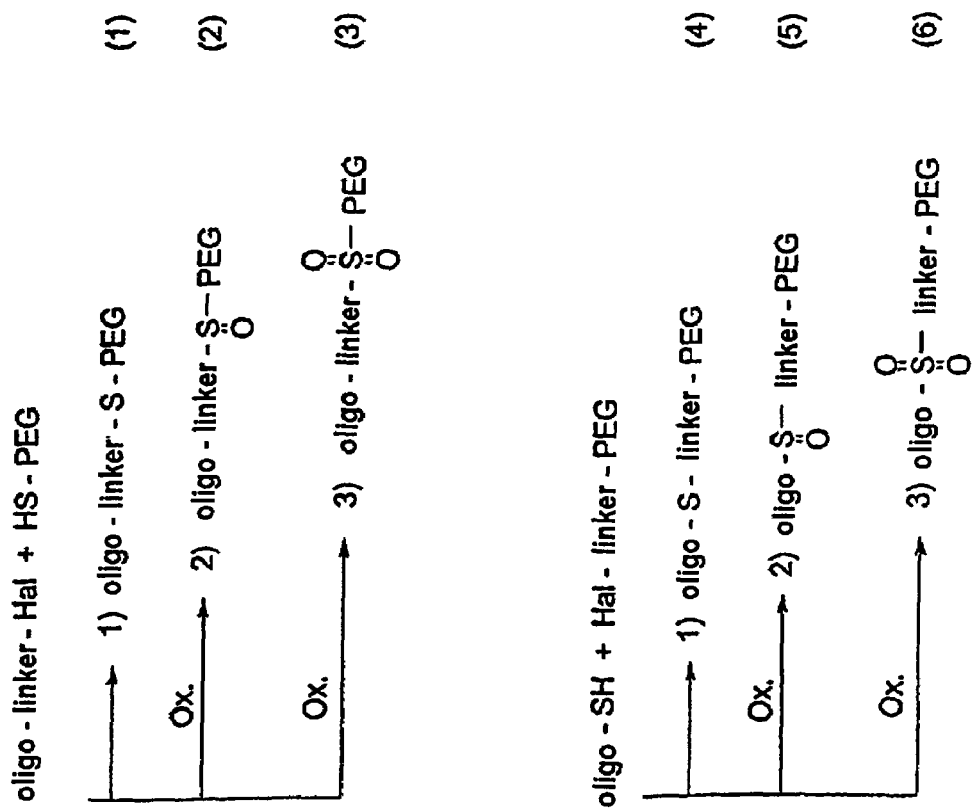
Figure 9:
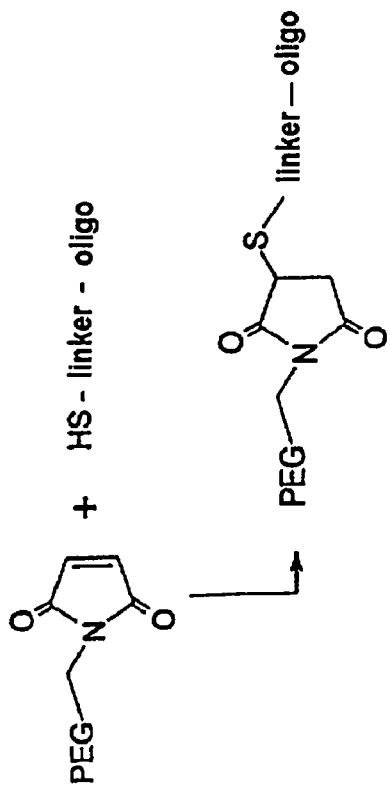
FIG. 9 shows the reaction of the PEG provided with a maleimide group with a L-nucleic acid, there referred to as oligo, that has an linker carrying a thiol group. The reaction product is a thioether.
Figure 10:
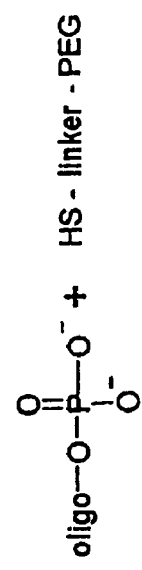
FIG. 10 shows the reaction of a L-nucleic acid carrying a phosphate group with a PEG, which is provided with a linker carrying a thiol group. The reaction product is a phosphothioate.
Figure 11:
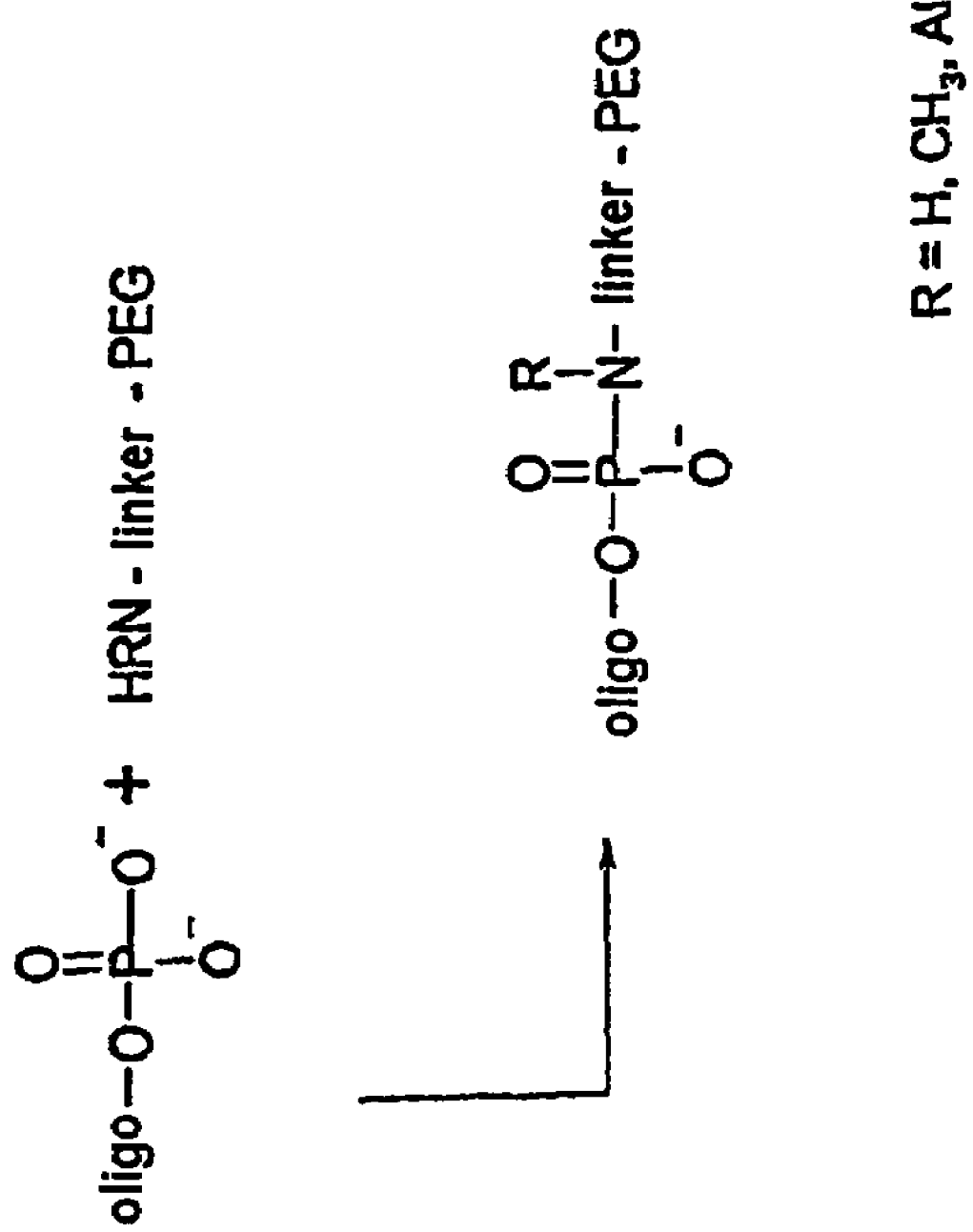

FIG. 11 shows the reaction of a L-nucleic acid provided with a phosphate residue, terminal if applicable, with a PEG, which is provided with a linker having an amine. The reaction product is a phosphoamidate. Regarding the residue R it applies what was elaborated on in the context of FIG. 6.

Figure 12:
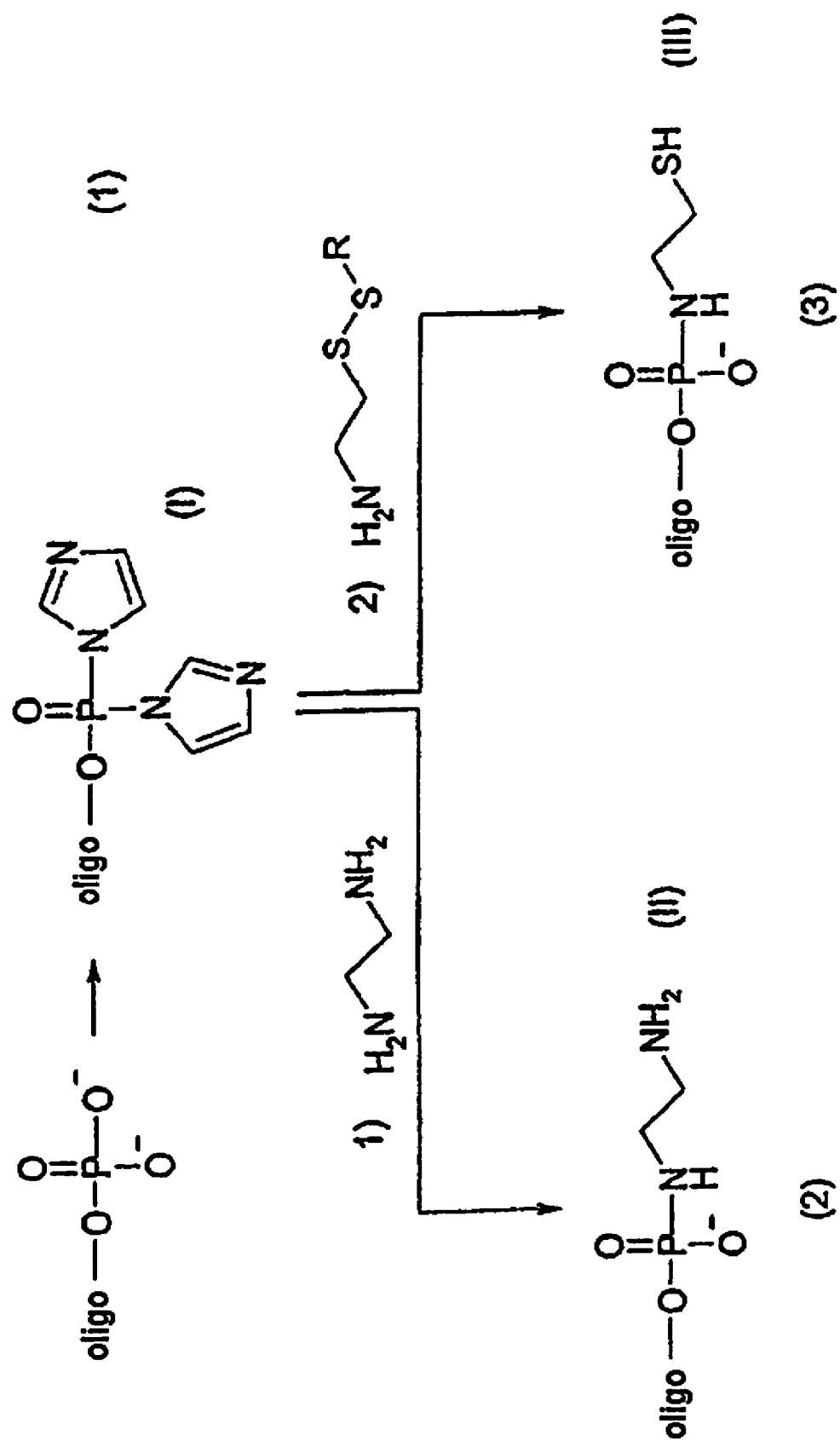

FIG. 12 shows the insertion of a reactive amino or thiol group, respectively, into a L-nucleic acid using an activate phosphate group, preferably a terminal phosphate group of the L-nucleic acid. Here, a phosphorimidazolide (I) is made in a first step, which leads to the formation of a 2-aminoethylene-1-phosphoramidate (II) in the case of reaction (2) using an ethylenediamine, or in the case of the reaction (3) using cysteamine to 2-thioethylene-1-phosphoamidate (III), respectively. The compounds according to (II) and (III) may be reacted thereupon with non-L-nucleic acids, particularly with those disclosed herein.

Figure 13:
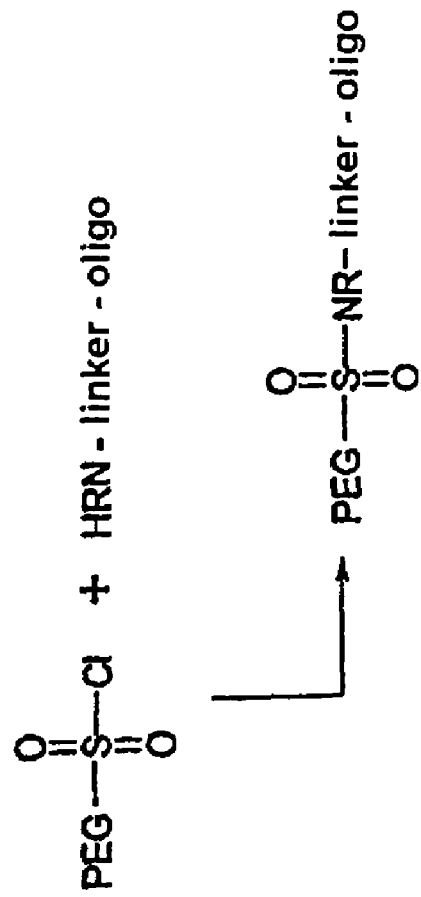

FIG. 13 shows the reaction of a PEG provided with a sulphonyl chloride group with a L-nucleic acid that has a linker carrying an amine group. The reaction product is a sulphonamide. Regarding the residue R it applies what was elaborated on in the context of FIG. 6.

Figure 14:
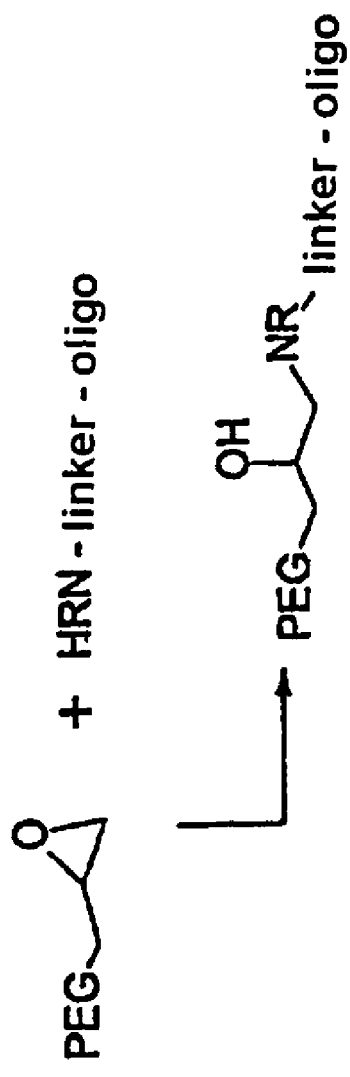

FIG. 14 shows the reaction of a PEG provided with an epoxide group with a L-nucleic acid that has a linker carrying an amine group forming an amine. Regarding the residue R it applies what was elaborated on in the context of FIG. 6.

Figure 15:
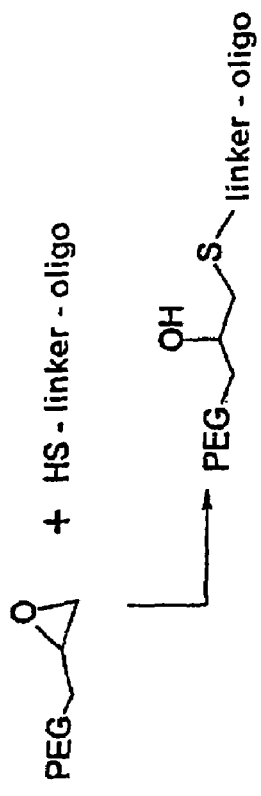

FIG. 15 shows the reaction of a PEG provided with an epoxide group with a L-nucleic acid that has a linker provided with a thiol group. The reaction product is a thioether.

Figure 16:
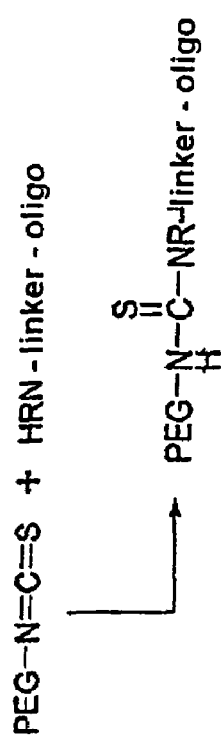

FIG. 16 shows the reaction of a PEG provided with an isothiocyanate group with a L-nucleic acid that has a linker carrying an amine group. The reaction product is an isothiourea. Regarding the residue R it applies what was elaborated on in the context of FIG. 6.

FIG. 17 shows the reaction of a PEG provided with an isocyanate group with a L-nucleic acid that has a linker carrying an amine group forming an isourea. Regarding the residue R it applies what was elaborated on in the context of FIG. 6.

FIG. 18 shows the reaction of a PEG provided with an isocyanate group with a L-nucleic acid that carries a free OH group, that may directly come from the L-nucleic acid, as for example from a phosphate group or the sugar moiety of the nucleoside, i.e. the positions 2'-OH, 3'-OH, or 5'-OH. Alternatively, the OH group may be linked to the L-nucleic acid via a suitable linker. The reaction product is a carbamate.

Figure 19:
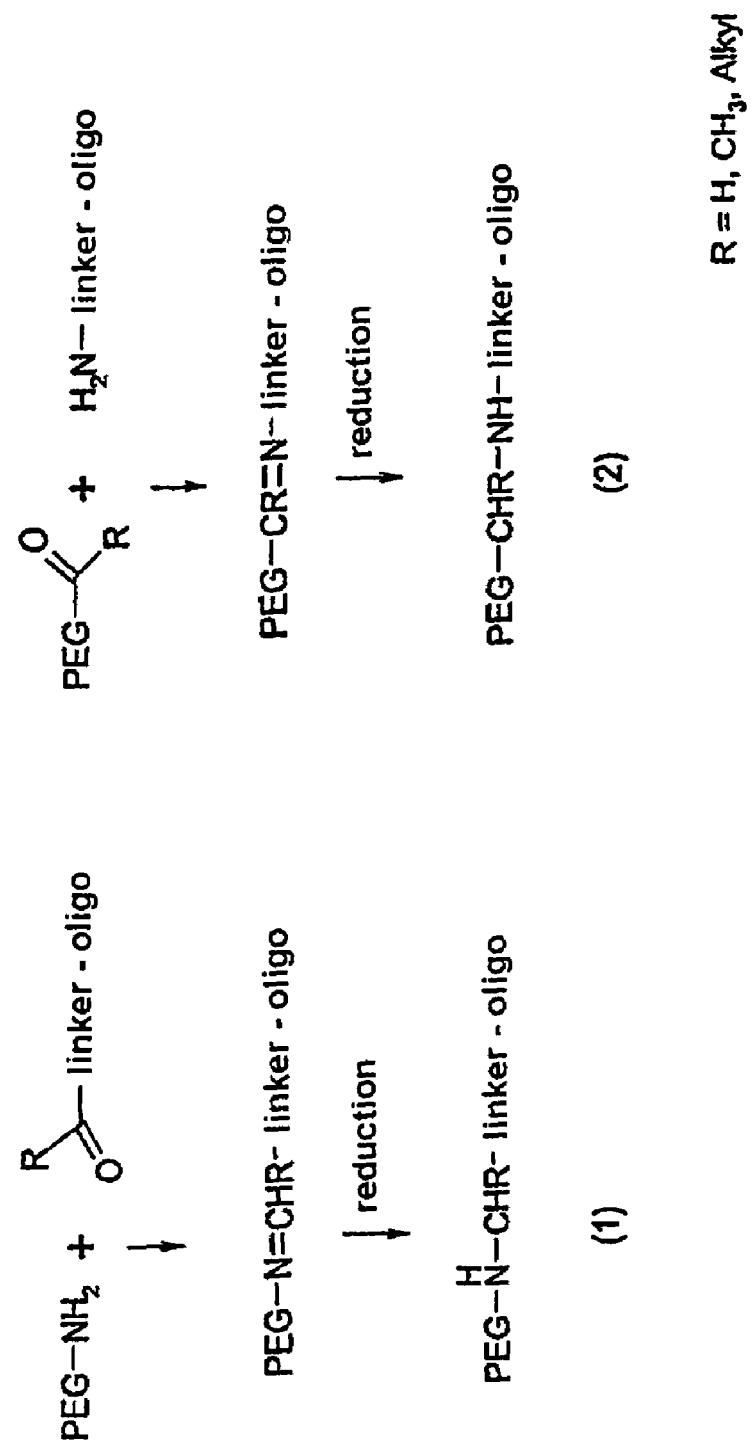

FIG. 19 shows the reaction of an aldehyde or keto group with an amino group, which is present in each case either at the non-L-nucleic acid part (reaction (1)), in the case shown at PEG; or at the L-nucleic acid part (reaction (2)). Preferably here, the L-nucleic acid part has a linker carrying the respective reactive group, i.e. the amino group or the carbonyl group. In the case of the reaction (1) the PEG carries a amino group, whereas the L-nucleic acid has a linker carrying the carbonyl group. The reaction product obtained directly, imine, is converted thereupon into an amine by reduction. In case of the reaction (2) the PEG carrying a carbonyl group is reacted with L-nucleic acid, that carries a linker having an amino group. The reaction product imine is reduced and leads to an amine. Regarding the residue R it applies what was elaborated on in the context of FIG. 6.

FIG. 20 shows the reaction of a PEG provided with a thiol group with a L-nucleic acid carrying a linker provided with a thiol group as well. The reaction product is a modified L-nucleic acid, that has a disulphide group between the PEG and the L-nucleic acid, strictly speaking the linker attached to it.

FIG. 21 shows the reaction of a PEG provided with a hydrazine group with a L-nucleic acid that carries a linker comprising a carbonyl group. In a fist step of the reaction a hydrazone is obtained, which is thereupon converted reductively into a substituted hydrazine. Regarding the residue R it applies what was elaborated on in the context of FIG. 6.

Figure 22:
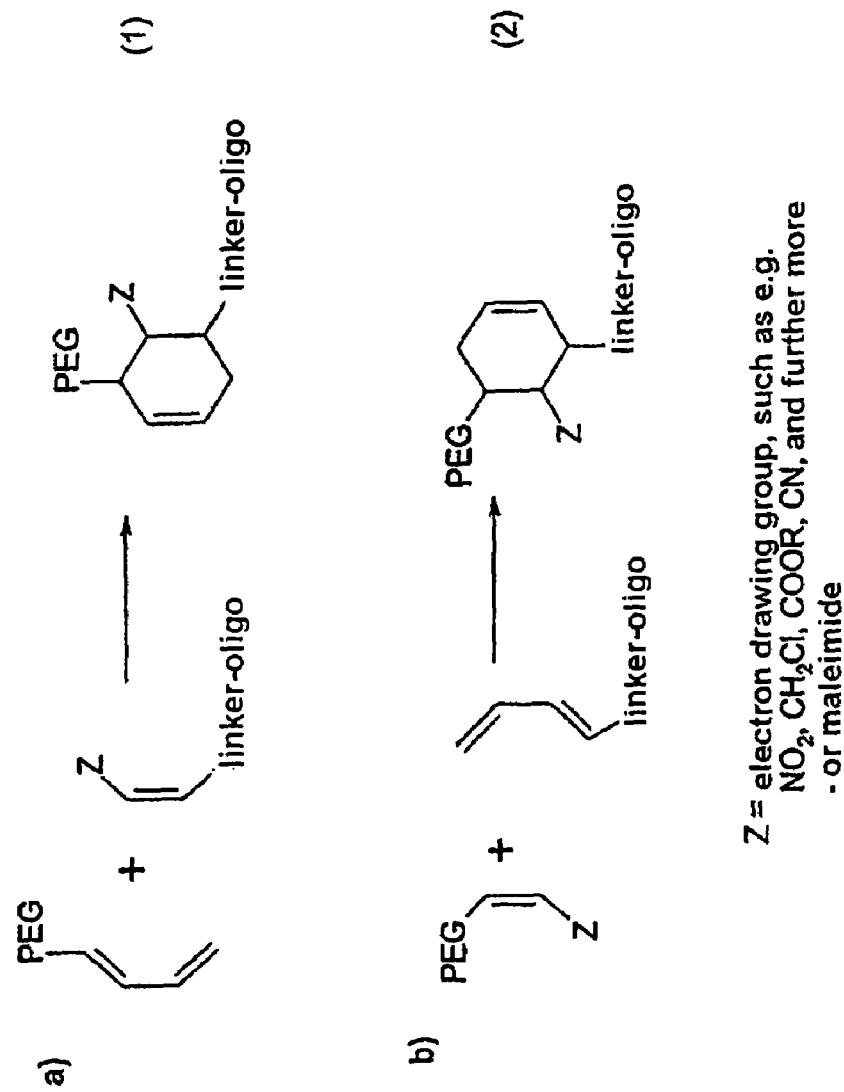

FIG. 22 shows in reaction (1) the conversion of a PEG provided with a conjugated diene with a L-nucleic acid that carries a linker with a so-called dienophilic group. The dienophile consists of a C—C-double bond, which in turn has a substituent Z comprising an electron-withdrawing group. These may be preferably $NO_2$, $CH_2Cl$, COOR, CN or maleimide. Regarding the residue R it applies what was elaborated on in the context of FIG. 6. Due to this reaction the formation of a modified L-nucleic acid occurs that has a hexeneyl group between the PEG and the L-nucleic acid provided with a linker. The Diels-Alder reaction shown in reaction (2) starts with a PEG which has a dienophile with-a substituent Z that reacts with a L-nucleic acid comprising a linker which carries a conjugated diene. Regarding the substituent Z it applies what was elaborated on, in the context of reaction (1). The reaction product in this reaction (2) is also a L-nucleic acid conjugate linked via a hexeneyl group.

FIG. 23 shows the structure of the branched and linear mPEG-NHS ester that were used.

FIG. 24 shows in (1) the basic assembly of an abasic L-nucleoside, which instead of the nucleobase may have either a hydrogen atom or one or more optionally different linker structures. Here R' denotes a L-nucleic acid or a L-polynucleotide, OH or phosphate, R" a L-nucleic acid or a L-polynucleotide, OH or phosphate and X=H, OH, OMe, OEt, $NH_2$. The residue R denotes either the hydrogen atom instead of the nucleobase or the linker, which may have the structural formulas shown in (2) to (8), wherein Z=$CH_2$, O, NH, NR, S and n may be an integer between 1 and 20. The functional group $X_1$ is preferably selected from the group that has HO, $H_2N$, HRN, HS, SSR, Hal, CHO, COOH, COOR, COHal.

Figure 25:
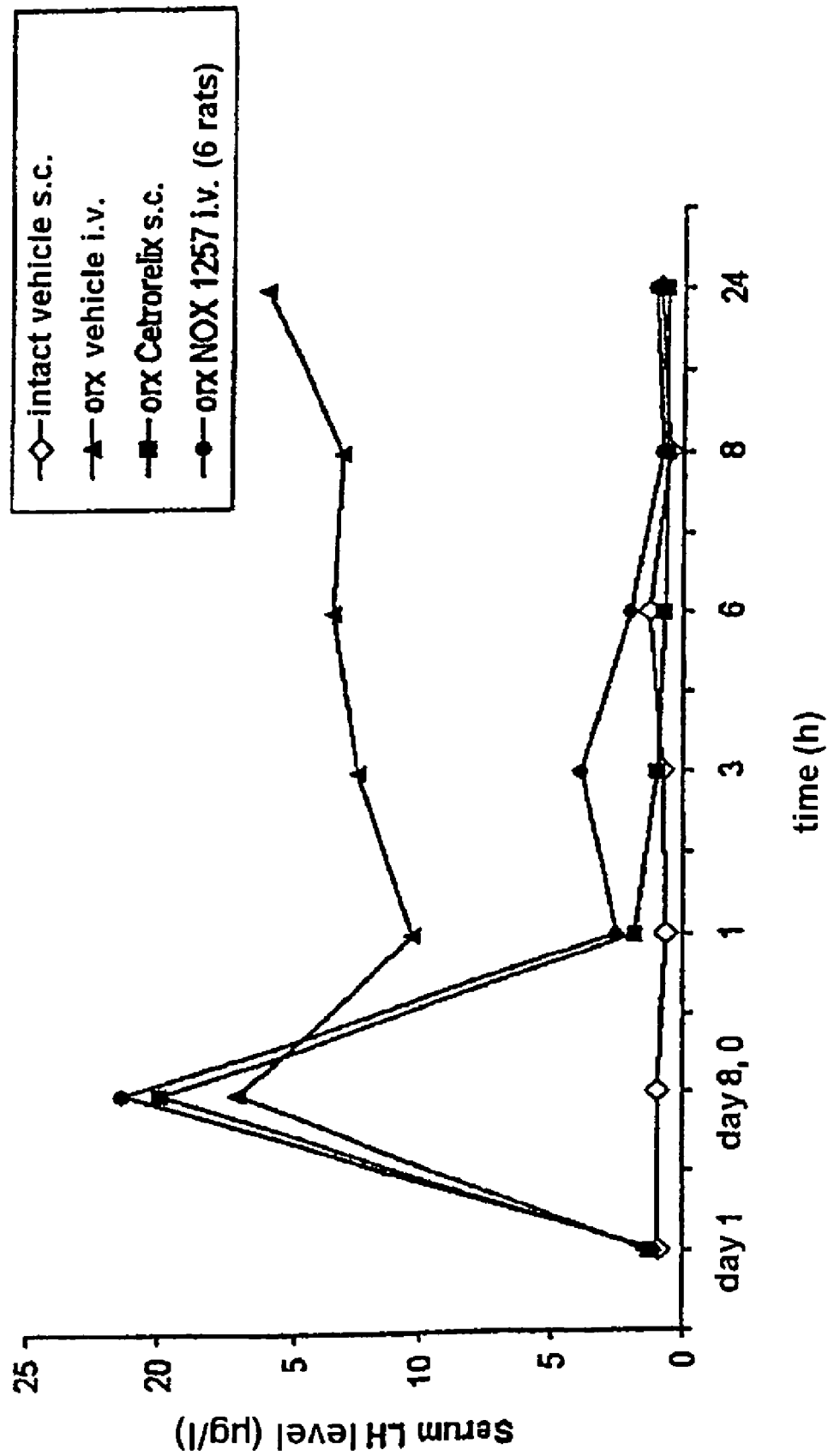

FIG. 25 shows an activity test of a PEGylated DNA spiegelmer binding GnRH in male orchidectomised rats.

Figure 26A:
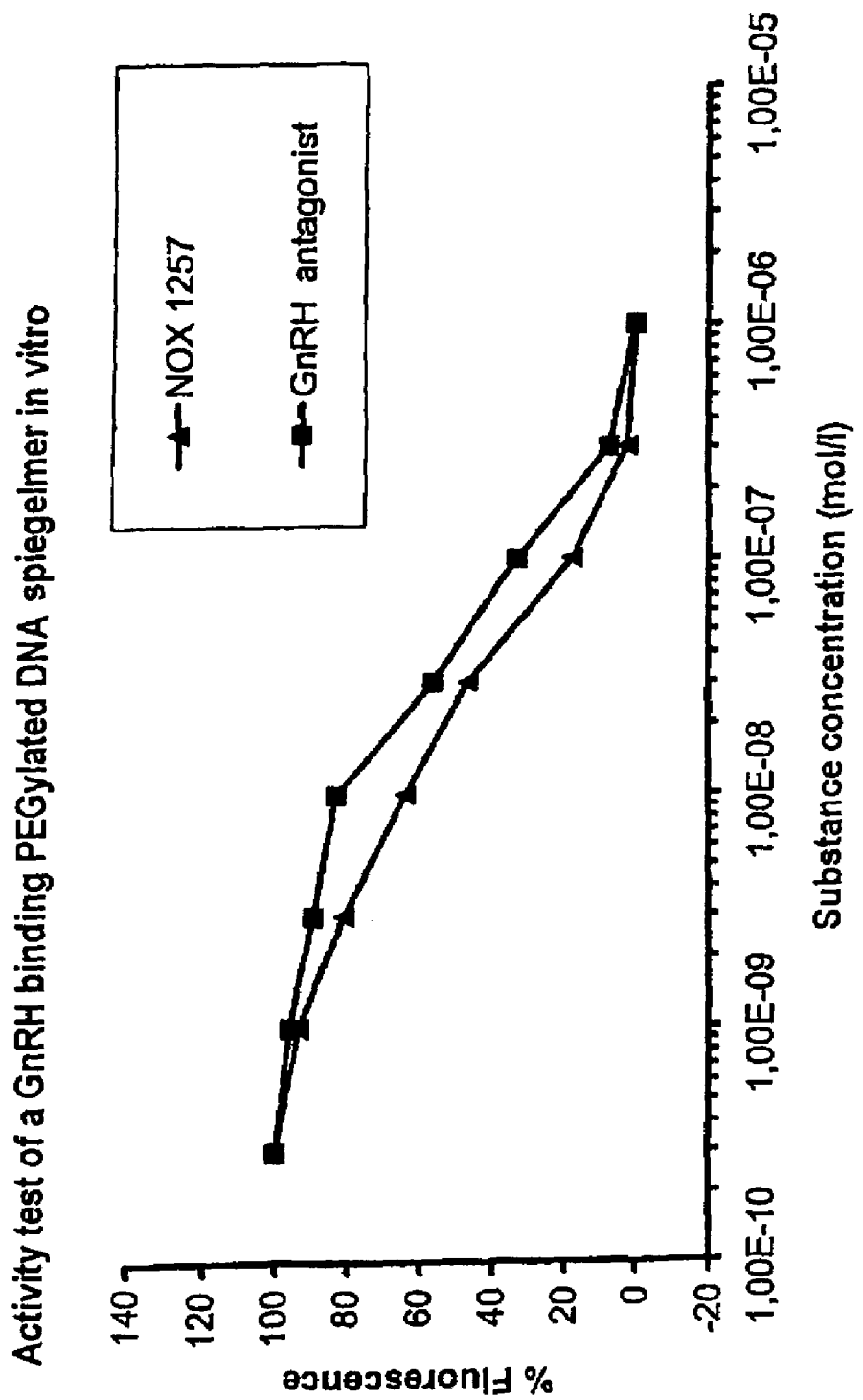

FIG. 26a shows an activity test of a PEGylated DNA spiegelmer binding GnRH in vitro.

Figure 26B:
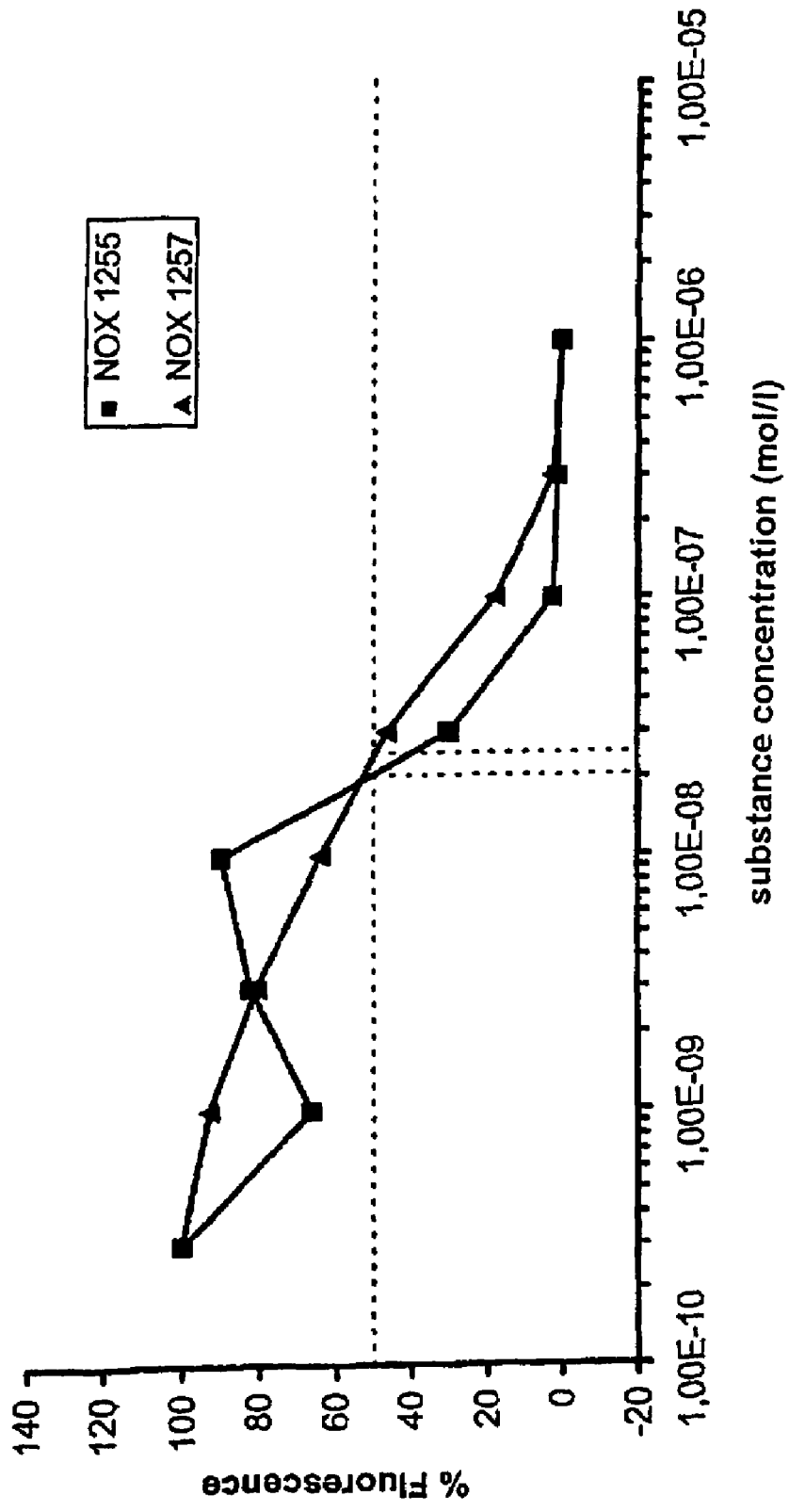

FIG. 26b shows an activity test of a non-PEGylated and PEGylated DNA spiegelmer binding GnRH in vitro.

Figure 27:
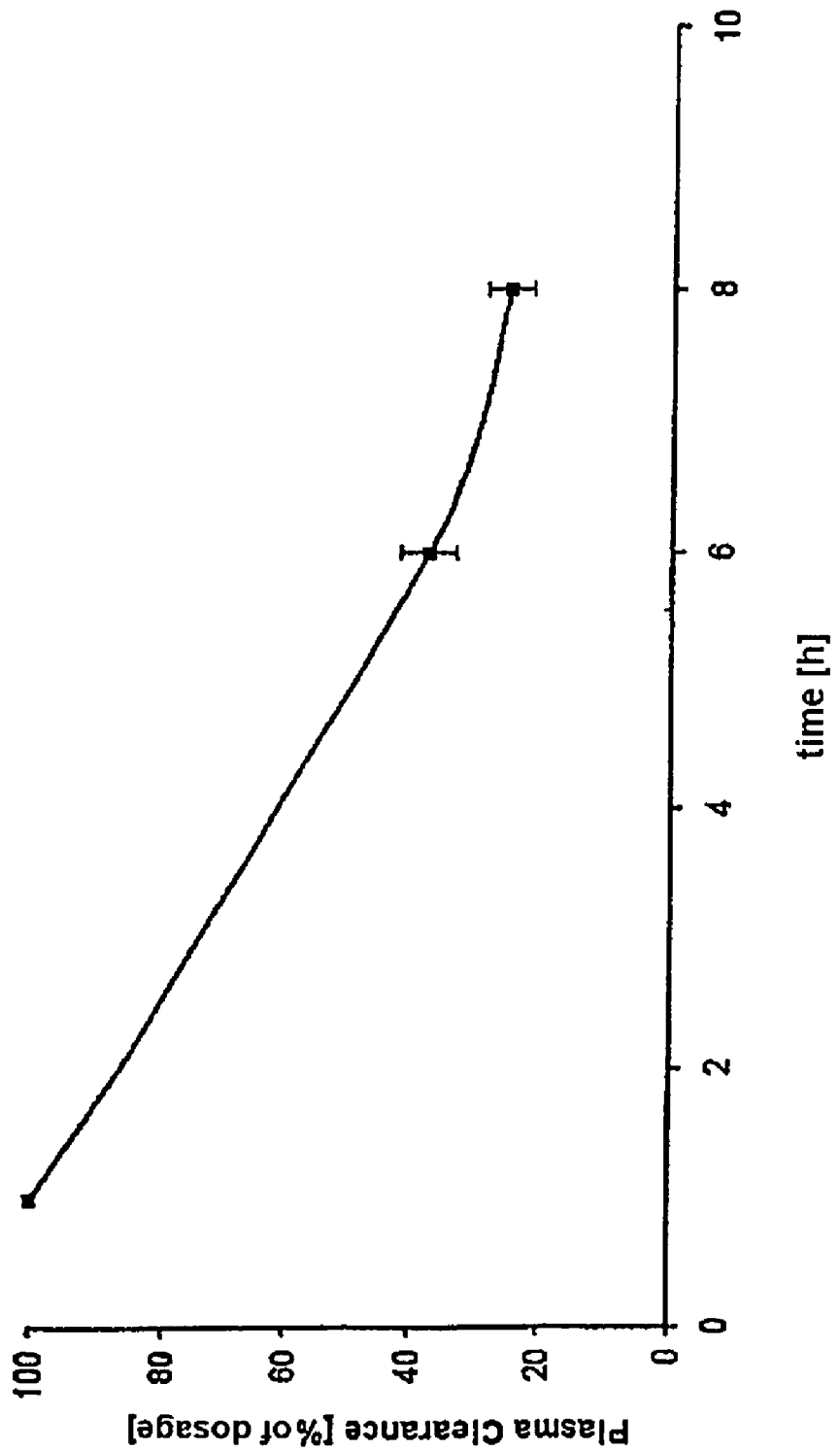

FIG. 27 shows the pharmacokinetics of a PEGylated DNA spiegelmer binding GnRH in rats.

Figure 28A:
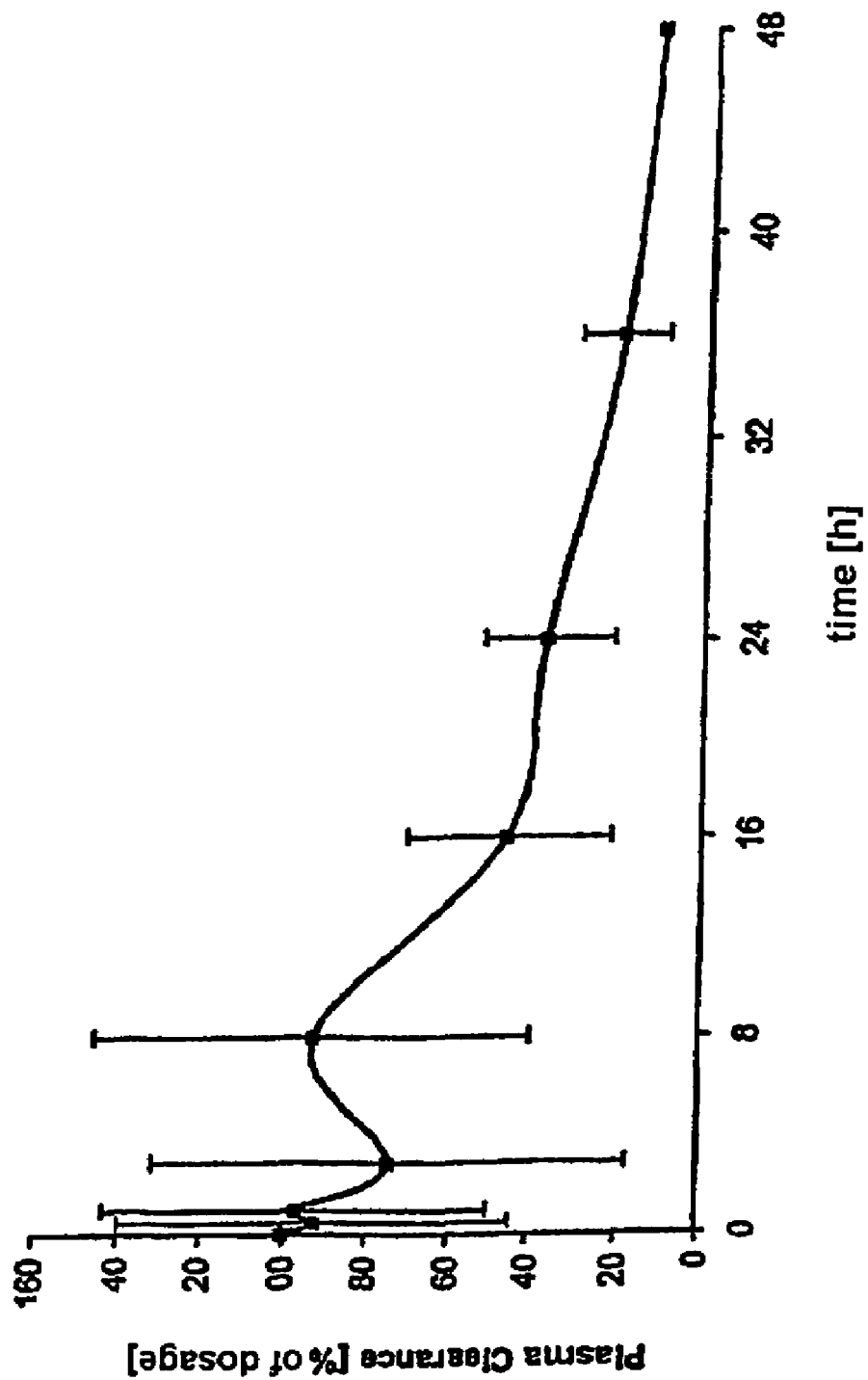

FIG. 28a shows a pharmacokinetical profile of PEGylated L-RNA after intravenous dose in rats.

Figure 28B:
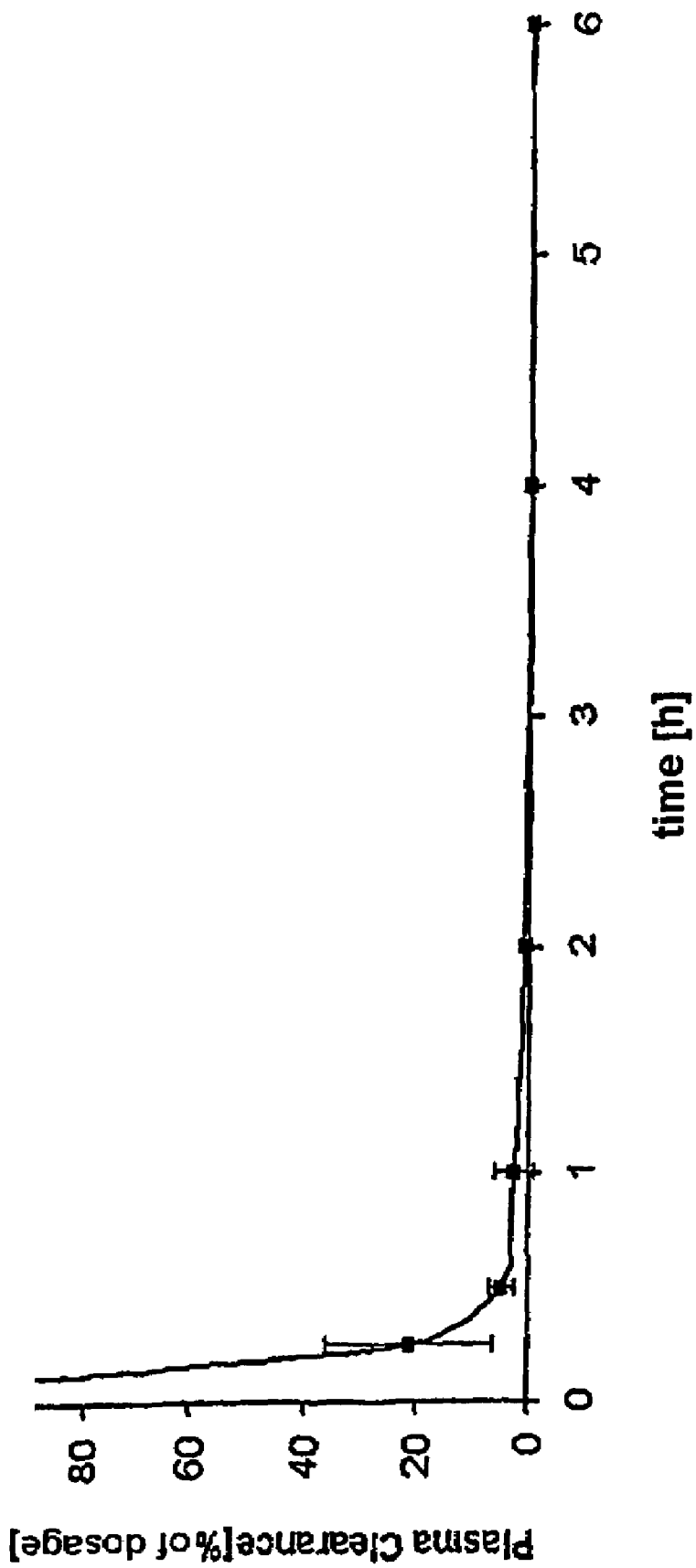

FIG. 28b shows a pharmacokinetical profile of non-PEGylated L-RNA after intravenous dose in rats.

Figure 28C:
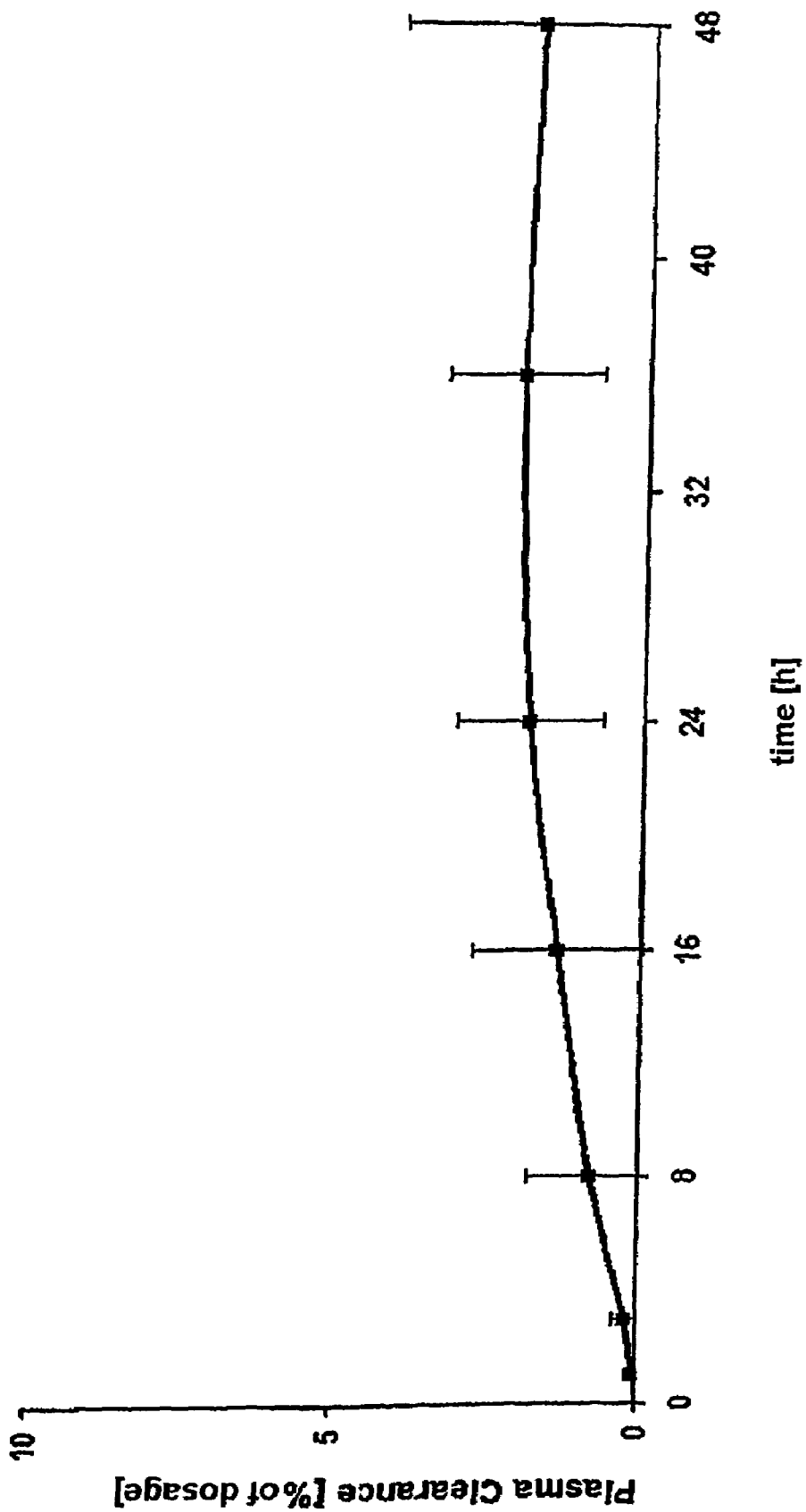

FIG. 28c shows a pharmacokinetical profile of PEGylated L-RNA after subcutaneous dose in rats.

Figure 28D:
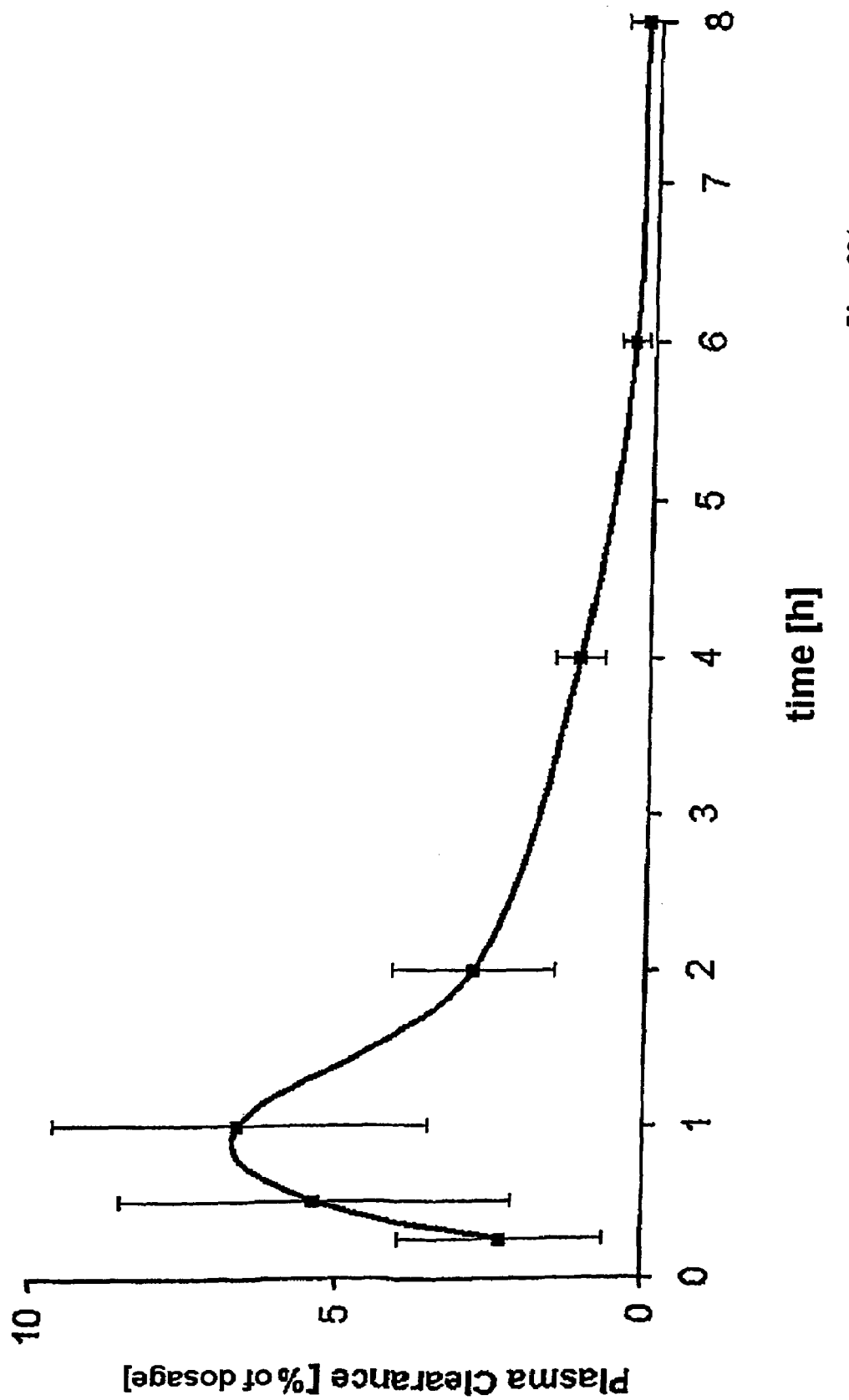

FIG. 28d shows a pharmacokinetical profile of non-PEGylated L-RNA after subcutaneous dose in rats.

Figure 29:
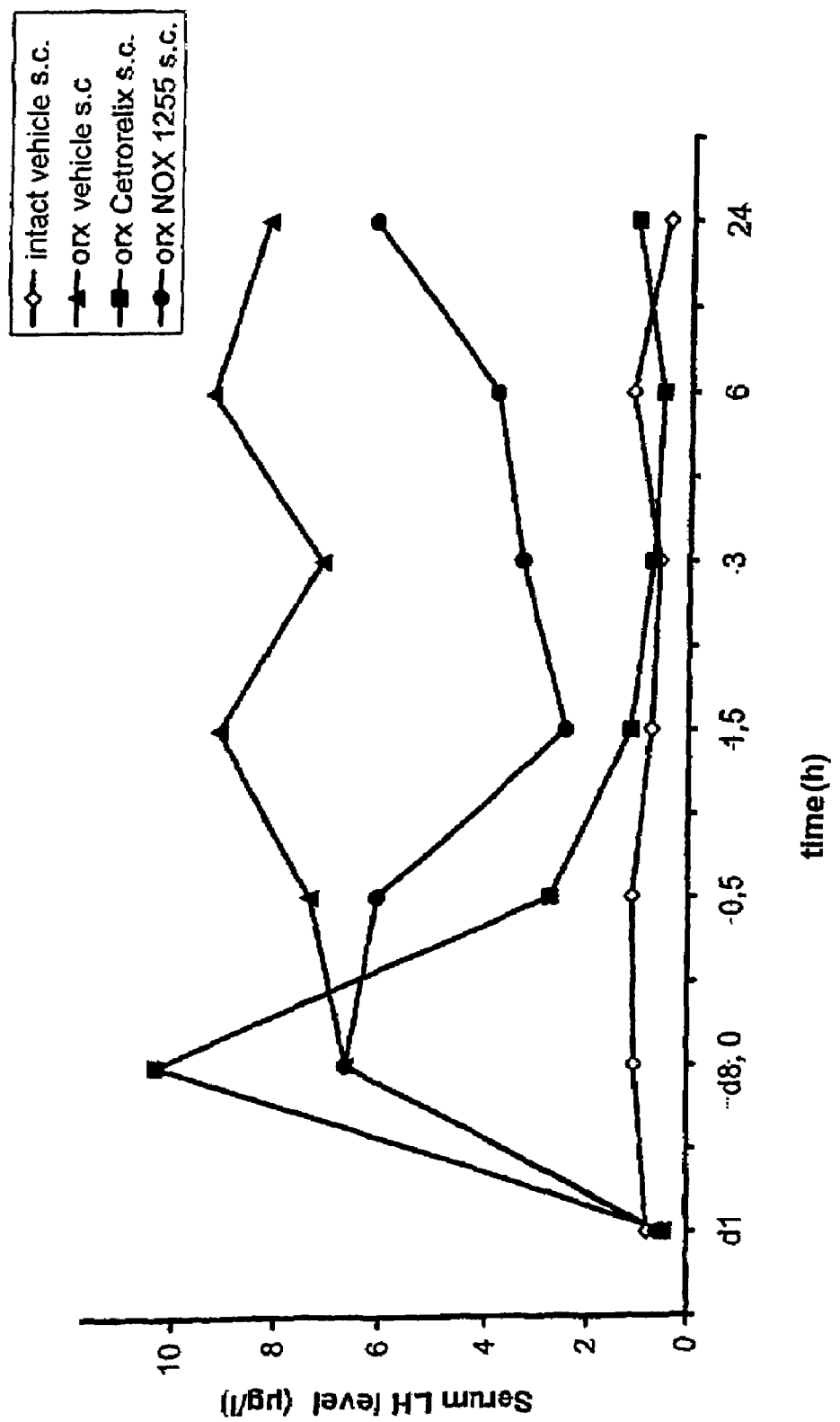

FIG. 29 shows an activity test of a DNA spiegelmer binding GnRH in male orchidectomised rats in vivo.

EXAMPLE 1

Synthesis of PEG Conjugates of L-nucleic Acids

The conditions for the synthesis of PEG conjugates of L-nucleic acids were examined starting from the L-nucleic acid depicted in SEQ ID NO: 2 and PEG, wherein the PEG was modified such that it was present either as a NHS ester or as a primary amine for the coupling onto an amine and a phosphate, respectively. It was proceeded in a way that the nucleic acid was dissolved in an aqueous system. The pH was adjusted to pH 6.5-9.0 by different buffers or bases like, for example $NaHCO_3$, $NaH_2PO_4/Na_2HPO_4$, HEPES, MOPS, $NH_4OAc$, triethylamine. The influence of addition of different organic solvents, as for example DMF, DMSO, acetonitrile and others was tested, wherein the portion of the organic solvent was varied between 0-100%. Subsequently the addition of different PEG derivatives occurred, as for example branched $mPEG_2$-NHS ester, linear mPEG-NHS ester or mPEG-$NH_2$ (Shearwater Corporations) of different molecular weights between 10,000 Da und 40,000 Da. The addition of PEG-NHS ester may be done in different ways. Thus, PEG-NHS ester may be dissolved for example in an acid of low concentration such as, for example 0.01 N HC1, or may be added in drops being dissolved in an organic solvent such as DMF or added as a solid. The preferred way of adding PEG-NHS is as a solid in portions. Further, the influence of the reaction temperature between 4° C.-65° C. was tested. As nucleic acids were used nucleic acids with the following sequence 5'-$NH_2$-TAT TAG AGA C-3' (SEQ ID NO: 2), and 5'-$PO_4$-TAT TAG AGA C-3' (SEQ ID NO: 3) as well as the nucleic acid according to SEQ ID NO: 1. The yields of the reactions summarised above were between 5-78%.

The preferred variant of reaction was the addition of two equivalents each of solid PEG-NHS ester in intervals of around 30 minutes, six times alltogether, to a nucleic acid dissolved in a solvent consisting of 60 parts $H_2O$ and 40 parts DMF adding $NaHCO_3$ (0.2 M), a pH of 8.0 and 37°. The reaction conditions lead to a yield of 78%.

EXAMPLE 2

Synthesis of a PEG Conjugate of a L-Nucleic Acid Phosphoamidate

Starting from a L-nucleic acid with the sequence 5'-$PO_4$-TAT TAG AGA C-3' (SEQ ID NO: 3) a corresponding phosphoamidate PEG conjugate was made. The L-nucleic acid (10 OD) was reacted with PEG-$NH_2$ (20,000 Da, linear, 1-10 equivalents) in aqueous solution with EDCI at 50° C. to a PEG conjugate of a L-nucleic acid phosphoamidate. The analysis and purification was done analogously to that of the PEGylation of L-nucleic acids with PEG-NHS, as described in example 1. The reaction conditions were not optimised and led to a yield of <8%.

EXAMPLE 3

PEGylation of a GnRH Spiegelmer Ligand

The peptide hormone GnRH I (gonadotropin releasing hormone, gonadoliberine), which is generally referred to as GnRH, is a dekapeptide made in the hypothalamus which stimulates the secretion of the gonadotropin hormones luteinising hormone and follicle stimulating hormone (FSH) by the pituitary gland. GnRH is secreted from the neurons of the hypothalamus in a pulsating manner and then binds to a receptor on the cell surface of the pituitary gland. The ligand receptor complex is internalised, whereby a release of FSH and LH occurs, which in turn stimulate the production of sexual hormones such as estrogen, progesteron or testosteron. A spiegelmer, i.e. a L-nucleic acid could be produced that binds specifically to GnRH and has the following sequence:

```
                                            (SEQ ID NO: 1)
5'-CCA AGC TTG CGT AAG CAG TCT CCT CTC AGG GGA GGT

TGG GCG GTG CGT AAG CAC CGG TTT GCA GGG G-3'
```

The synthesis of the spiegelmer of the sequence shown above was performed on an Amersham Pharmacia Biotech Oligopilot II DNA synthesiser in 780 µMol scale on a 1,000 Å CPG solid phase (Controlled Pored Glass) according to the 2-cyanoethyl-phosphoramidit chemistry (Sinha et al. NAR, 12, 1984, p. 4539ff). Subsequently, a 6-(monomethoxytrity-lamino)-hexyl-(2-cyanoethyl)-(N,N-diiosopropyl)-phosphoramidit was linked to the 5' end of the spiegelmer (5'-MMT-aminohexyl spiegelmer), to allow the post-synthesis conjugation with PEG.

After completion of the synthesis the 5'-MMT aminohexyl spiegelmer was cleaved from the solid phase by an 8 hour incubation in 33% ammonia solution at 65° C., and deprotected completely, afterwards concentrated to dryness, taken up into 10 mM NaOH and purified by means of RP-HPLC. The cleavage of the monomethoxytrityl protection group occurred with 0.4% trifluoracetic acid (TFA) in 30 min at RT. TFA was removed by twofold coevaporation with ethanol and the 5'-aminohexyl spiegelmer according to SEQ ID NO: 1 was purified by precipitation in ethanol (yield: 5,000 OD, 7.5 µmol). The product peak was collected and desalted by means of size-exclusion chromatography via a Sephadex G10 column or by ultrafiltration (Labscale TFF System, Millipore).

The GnRH spiegelmer 5-amino-modified in such a way (5,000 OD, 7.5 µmol) was prepared in 0.2 M NaHCO$_3$, pH 8.5/DMF 60:40 (v/v) (125 mL), warmed to 37° C. and powdery N-hydroxysuccinimidyl (NHS) activated ester of branched 40.000 Da poly(ethylen)glycol was added in portions (2 eq (equivalents) every 30 min, alltogether 12 eq, (6×600 mg, 180 µmol). The progress of the reaction was monitored by analytical gelectrophoresis (8% polyacrylamide, 8.3 M urea). The raw product was purified initially by ion exchange HPLC from excess PEG (Source Q 30; solvent A: H$_2$O, solvent B: 2 M NaCl; low rate 20 mL/min; loading of the column and elution of free PEG with 10% B; elution of the PEG-GnRH spiegelmer conjugate with 50% B), subsequently GnRH spiegelmer PEGylated by RP-HPLC was separated from non PEGylated GnRH spiegelmer (Source RPC 15; solvent A: 100 mM triethylammonium acetate (TEAA), solvent B: 100 mM TEAA in H$_2$O/acetonitril 5:95; flow rate 40 mL/min; loading of the column with 10% B; gradient from 10% to 70% B in 10 column volumes, elution of PEG-GnRH spiegelmer at 45-50% B), salt exchanged (Source Q 30; solvent A: H$_2$O, solvent B: 2 M NaCl; flow rate 20 mL/min; loading of the column and elution of free PEG with 10% B; elution of PEG-GnRH spiegelmer with 50% B) and subsequently desalted by gel filtration (Sephadex G10; solvent H$_2$O; flow rate 5 mL/min) or ultrafiltration (Labscale TFF System, Millipore). By lyophilisation the desired product was obtained as a white powder (3.900 OD, 375 mg, 78%).

Analogously, further nucleic acids including the sequence according to SEQ ID NO:1 linked with different PEG (linear 10,000 Dalton, linear 20,000 Dalton, branched 20,000 Dalton, linear 35,000 Dalton), and purified.

EXAMPLE 4

Synthesis of FITC Conjugates of L-Nucleic Acids: Coupling of Fluorescein Isothiocyanate onto a GnHR Spiegelmer with a 5'NH$_2$—C$_6$ Linker The 5'amino-modified GnRH spiegelmer made according to example 3 was prepared in 0.5 M NaHCO$_3$ pH 8.5, warmed to 65+ C. and an excess of fluorescein isothiocyanate (FITC, 10 eq) was added to the reaction mixture. The reaction was monitored by means of analytical RP-HPLC. It was shaken for 48 h at 65° C., excess FITC separated by Centri-Spin10 (Princeton Separations) and the fluorescein labeled L-nucleic acid was purified with RP-HPLC. Lyophilisation delivered the desired product as a yellowish powder in quantitative yield.

EXAMPLE 5

Activity Test of a GnRH Binding, PEGylated DNA Spiegelmer in vivo in Male Orchidectomised Rats Male rats were orchidectomised, whereby the LH level of the rats increased steadily during the following eight days due to the missing testosteron feedback signal. On day 8 the PEG-GnRH DNA spiegelmer, i.e. the conjugate from PEG and GnRH spiegelmer, was administered intravenously to seven rats (150 mg/kg). Blood samples were taken on day 0 (prior to the orchidectomy), on day 8 (0 hours prior to i.v. application of the PEG-GnRH spiegelmer), 0.5 h, 1.5 h, 3 h, 6 h as well as 24 h post i.v. application and the respective LH level determined using radioimmunoassay (RIA). In parallel, only the vehicle (PBS buffer, pH 7.4) i.v. as a negative control was administered to seven male orchidectomised rats, and the standard antagonist Cetrorelix (100 µg/kg) s.c. as a positive control to seven male orchidectomised rats. The result is shown in FIG. 25.

With the exception of the negative control (in FIG. 25 depicted as triangles) there is a LH level even after 24 h under the influence of the PEG-GnRH spiegelmers, that is comparable to that of the non-orchidectomised rats, and those rats, respectively, which had received the standard antagonist Cetrorelix. This proves the suitability of the PEG-GnRH DNA spiegelmer, to influence lastingly the effect of the GnRH over an extended period of time. That the effect of the PEG-GnRH DNA spiegelmer described above is due to the PEGylation of the GnRH spiegelmer results from the fact that upon application of the GnRH spiegelmer without the corresponding modification with subcutaneous application of 100 mg/kg a reduction of the activity of the GnRH speigelmer could be observed already after a few hours. The result is shown in FIG. 29 as well.

EXAMPLE 6

Activity Test of GnRH Binding, PEGylated and Non-PEGylated DNA Spiegelmers in CHO Cells in vitro The cell culture study described herein was performed on Chinese Hamster Ovary (CHO) cells, which express the human receptor for GnRH. Here the intracellular release of Ca²⁺ ions was measured, since this release, important for the signal transduction, occurs after formation of the agonist receptor complex. The $Ca^{2+}$ level was then deterined by a $Ca^{2+}$ sensitive fluorescence dye. The PEG-GnRH DNA spiegelmer and the GnRH spiegelmer, respectively, was to capture the agonist GnRH and thus inhibit its binding to the receptor on the cell membrane. It was done experimentally such that the agonist GnRH (2 nM) was preincubated for 20 min with the GnRH spiegelmer and the PEG-GnRH DNA spiegelmer, respectively, in a concentration range of 100 pM bis 1 µM. This solution each was given to the CHO cells loaded with fluorescence dye, and the respective $Ca^{2+}$ concentration determined with a Fluroescence Imaging Plate Reader (FLIPR). The result of the PEG-GnRH DNA spiegelmer (filled triangles) and of a standard antagonist (filled squares), used here as a positive control, is shown in FIG. 26a.

The concentration dependant determination resulted in a sigmoidal activity curve, which indicates that the native, i.e. the non-modified GnRh spiegelmer (filled squares), as well as GnRH-DNA spiegelmer modified with PEG (filled triangles) were able to inhibit the formation of the GnRH receptor complex at 100%. The $IC_{50}$ was 20 nM for the GnRH spiegelmer und 30 nM for the PEG-GnRH DNA spiegelmer (FIG. 26b).

EXAMPLE 7

Pharmacokinetics of a GnRH Binding PEGylated DNA Spiegelmer in Rats

Seven male Wistar rats (Tierzucht Schönwalde GmbH, Germany, weight: 250-300 g) were used for the determination of the phamacokinetical characteristics of the GnRH binding PEGylated DNA spiegelmer. The group was treated in parallel with the groups for the activity tests (see example 6), i.e. castrated after an adaption phase, and after another week the animals received a single dose of 800 nmol/kg PEG-GnRH DNA spiegelmer administered intravenously. The substance was dissolved in 1×PBS, pH 7.4 (stock solution: 1 mM).

For analysis blood samples were taken prior to substance dose (0 h) as well as 1 h, 6 h, and 8 h post substance dose, and analysed as EDTA plasma.

From the plasma GnRH binding PEGylated DNA spiegelmer was extracted by solid-phase extraction aided by weak anion exchangers. For this 50 µl EDTA plasma each were dissolved in buffer A (50 mM $NaH_2PO_4$, pH 5.5; 0.2 M $NaClO_4$; 20% (v/v) formamide und 5% (v/v) acetonitril) in a total volume of 1 ml and stored at 4° C. over night or at −20° C. for 4 days maximum, respectively, until extraction. Frozen samples were thawed for at least 2 h at room temperature, mixed and subsequently centrifuged.

For solid-phase extraction dimethylaminopropyl-anion exchanger columns (DMA 3 ml/200 mg column material, Macherey & Nagel, Düren) on a Baker spe-12G vakuum apparatus (Mallinckrodt Baker, Griesheim) was used. The buffers used consisted of: buffer A (50 mM $NaH_2PO_4$, pH 5.5; 0.2 M $NaClO_4$; 20% (v/v) formamide und 5% (v/v) acetonitril and buffer B (80 mM $NaH_2PO_4$, pH 6.0; 50 mM $Na_2HPO_4$, 2 M $NaClO_4$; 20% (v/v) formamide und 5% (v/v) acetonitril), wherein the two buffers A and B were mixed in a specific ratio for the preparation of the wash and the elution buffer, such that the desired salt concentrations were achieved. The anion exchangers were flushed with 2 ml of buffer A. The samples were added applying −100 mbar and washed with 2 ml of buffer A as well as 2 ml of wash buffer (0.4 M $NaClO_4$). After drying the column material for 5 min by applying −200 mbar, the PEGylated GnRH binding DNA spiegelmer was eluted with 3×0.5 ml elution buffer (0.9 M $NaClO_4$), wherein the buffer was heated to 70° C. prior to elution. The eluates were stored at 4° C. until gel filtration.

As an internal standard an 30 mer DNA spiegelmer had been added to the samples prior to extraction, which was bound to a 40 kDa polyethylenglycol molecule (PEG) at the 5'-end. The internal standard was brought with buffer to a volume of 360 µl at a concentration of 1 µg/µl, and 10 µl each thereof were added to each sample.

To desalt the samples prior to the HPLC analysis NAP-25 columns (Amersham Pharmacia Biotech) were used. The eluates obtained were dried under vacuum and dissolved in 100 ml of 10 mM Tris-HCl, pH 8.0.

The identification and quantification of the PEGylated spiegelmer was done by means of anion exchange chromatography using a Waters Alliance 2695 HPLC system and detection at 254 nm. The conditions were as follows: precolumn: DNAPac PA-100 (504 mm, Dionex) main column: DNAPac PA-100 (2504 mm, Dionex) eluent A: 10 mM NaOH, 1 mM EDTA, 10% (v/v) acetonitril in water eluent B: 375 mM $NaCl_4$ in eluent A temperature: 25° C. injection volume: 20 µl gradient und flow rates: 0-1 min 10% eluent B with 0.5 ml/min; 1-2 min 10% eluent B with 2 ml/min; 2-3 min 30% eluent B with 2 ml/min; 3-13 min 60% eluent B with 2 ml/min; 13-19 min 10% eluent B with 2 ml/min.

The concentration of PEGylated GnRH binding DNA spiegelmer at the different points in time of sampling is shown in FIG. 27. The half time of the PEGylated GnRH binding DNA spiegelmer upon intravenous injection is about 4 hours in rats.

EXAMPLE 8

Pharmacokinetics Profile of Unmodified and PEGylated L-RNA in Rats nucleotide sequences:

```
                                              (SEQ ID NO: 4)
L-RNA, 40mer (NOX_M039)
5' uaa gga aac ucg guc uga ugc ggu agc gcu gug cag
agc u 3'

(SEQ ID NO: 5)
40 kDalton PEG-L-RNA, 40 mer (NOX_M041)
PEG 5'uaa gga aac ucg guc uga ugc ggu agc gcu gug
cag agc u 3'
```

The pharmacokinetical profile of the non-PEGylated L-RNA (NOX_M039) and PEGylated L-RNA (NOX_M041) was examined in male rats (CD®, Charles River Germany GmbH; weight 280-318 g). After a 7 day settling-in period, 3 animals per substance received a single dose of 150 mmol/kg applied intravenously. 4 rats each per substance received 150 mmol/kg each as a single subcutaneous dose. The substances were dissolved in 1×PBS pH 7.4 (stock solution: 383 µM). After intravenous dose blood samples were taken for the unmodified L-RNA prior to substance application (0 min) and 5 min, 15 min, 30 min, 1 h, 2 h, 4 h, 6 h after substance application and transferred into EDTA Eppendorf tubes for analysis. After intravenous dose blood samples were taken for the PEGylated L-RNA prior to substance application (0 min) and 5 min, 30 min, 1 h, 3 h, 8 h, 16 h, 24 h, 36 h as well as 48 h after substance application and transferred into EDTA Eppendorf tubes for analysis. In subcutaneously treated animals blood samples were taken for the unmodified L-RNA prior to substance application (0 min) and 5 min, 15 min, 30 min, 1 h, 2 h, 4 h, 6 h after substance application and transferred into EDTA Eppendorf tubes for analysis. In subcutaneously treated animals blood samples were taken for the PEGylated L-RNA prior to substance application (0 min) and 5 min, 30 min, 1 h, 3 h, 8 h, 16 h, 24 h, 36 h and 48 h after substance application and transferred into EDTA Eppendorf tubes for analysis.

The amount of L-RNA and PEGylated L-RNA in the blood samples was examined by means of a hybridisation assay (see Drolet, D. W. et al. (2000) Pharmacokinetics and safety of an anti-vascular endothelial growth factor aptamer (NX1838) following injection into the vitreous humor of rhesus monkeys. Pharmaceutical Res 17 (12): 1503-1510.). The hybridisation assay is based on the following principle: the L-RNA molecule to be detected is hybridised to an immobilised L-DNA oligonucleotide probe (=capture probe; here: 5'-CCG CAT CAG ACC GAG TTT CCT TA T TTT TTT TT-(C7) NH2-3' (SEQ ID NO: 6)) and detected by a biotinylated detection L-DNA probe (=detector probe; here: 5'-(BB) TTT TTT TT A GCT CTG CAC AGC GCT-3' (SEQ ID NO: 7)). For this a streptavidine alkaline phosphatase conjugate is bound to the complex in a further step. After addition of a chemiluminescence substrate, light is generated and measured in a luminometer.

Immobilisation of the oligonucleotide probe: 100 g of the capture probe (0.75 pmol/µl in coupling buffer: 500 mM Na$_2$HPO$_4$ pH 8.5, 0.5 mM EDTA) per well were transferred into DNA BIND plates (COSTAR) and incubated over night at 4° C. Subsequently, it was washed with 3×200 µl coupling buffer each and incubated for 1 h at 37° C. with 200 µl blocking buffer (0.5% (w/v) BSA in coupling buffer) each. After renewed washing with 200 µl coupling buffer and 3×200 µl hybridisation buffer 1 (0.5×SSC pH 7.0, 0.5% SDS (w/v)) the plates may be used for detection.

Hybridisation and detection: a 20 pmol/µl solution of the detection L-DNA probe (=detector probe) in 10 mM Tris-Cl pH 8.0 was prepared. 10 µl EDTA plasma (or ddH$_2$O) were mixed with 90 µl hybridisation buffer 1 (0.5×SSC pH 7.0, 0.5% (w/v) SDS). Subsequently, 2 µl of the detector probe solution (20 pmol/µl) were added, mixed and centrifuged. A denaturing step at 95° C. for 10 min in the Thermocycler (MJ Research) followed. The batches were transferred into the DNA-BIND wells prepared accordingly (see above) and incubated for 2 h at 50° C. Thereafter washing steps followed: 2×200 µl hybridisation buffer 1 (0.5×SSC pH 7.0, 0.5% (w/v) SDS) and 3×200 µl 1×TBS/Tween 20 (20 mM Tris-Cl pH 7.6, 137 mM NaCl, 0.1% (v/v) Tween 20). 1 µl streptavidine alkaline phosphatase conjugate (Promega) was diluted with 5 ml 1×TBS/Tween 20. 100 µl of the diluted conjugate were added per well and incubated at room temperature for 30 min. Washing steps followed: 1×200 µl 1×TBS/Tween 20 and 3×200 µl 1×assay buffer (20 mM Tris-Cl pH 9.8, 1 mM MgCl$_2$). Finally, 100 µl CSPD "Ready-To-Use Substrate" (Applied Biosystems) were added, incubated 30 min at room temperature, and the chemiluminescence was measured in a POLARstar Galaxy multidetektion plate reader (BMG Labtechnologies).

The concentration-time-curves of the PEGylated L-RNA upon intravenous and subcutaneous dose are shown in FIG. 28a and FIG. 28c. The concentration profiles of the unmodified L-RNA upon intravenous and subcutaneous dose are shown in FIG. 28b and FIG. 28d. Upon intravenous dose the terminal half time is 50 minutes for the unmodified L-RNA. For the PEGylated substance, by contrast, a half time of around 18 hours results. Upon subcutaneous dose the terminal half time is 84 minutes for the unmodified L-RNA, for the PEGylated substance, by contrast, results a very long elimination phase.

Thus it is shown, that the modified L-nucleic acid according to the invention is of advantage in comparison with the unmodified L-nucleic acid. This advantage arises also with a view of the state of the art, described for example by Watson S. R. et al., Antisense nucleic acid drug dev. 10. 63-75 (2000). In this publication a 2'-F-modified aptamer is examined, which binds to L-selectin. The pharmacokinetical half time of the PEGylated 2'-F-aptamer (40 kDa PEG) administered intravenously in vivo in Sprague-Dawley rats is 228 min and is thus clearly shorter than those of the L-nucleic acids modified according to the invention.

EXAMPLE 9

General Method for the PEGylation of L-Ribonucleic Acids

A L-ribonucleic acid was generated for the examination of the pharmacological profile of unmodified and PEGylated L-RNA in rats. The L-RNA has the following sequence:

(SEQ ID NO: 4)
5'-UAA GGA AAC UCG GUC UGA UGC GGU AGC GCU GUG CAG

AGC U-3'

The synthesis of the L-RNA with the sequence shown above was performed on an ÄKTA Pilot 10 Synthesizer (Amersham Pharmacia Biotech, Uppsala, Sweden) in a 20 µM scale at a 1000 Å CPG solid phase according to the 2-cyanoethyl phosphoramidit chemistry. Subsequently, 6-(monomethoxytritylamino)-hexyl-(2-cyanoethyl)-(N,N-diiospropyl)-phosphoramidit was coupled to the 5'-end of the L-RNA (5'-MMT-aminohexyl-L-RNA) to allow the postsynthesis conjugation with PEG.

After completion of the synthesis the 5'-MMT-aminohexyl-L-RNA was cleaved from the solid phase by 30 min incubation in 41% methylamine solution at 65° C., and the nucleobases were deprotected completely. Deprotection of the 2'-position was done by incubation in 1.5 ml DMSO, 0.75 ml triethylamine (TEA) and 1 ml TEA 3HF for 2 h at 60° C. A first purification was done by means of RP-HPLC. The cleavage of the monomethoxytrityl protection group was carried out with 80% acetic acid in 70 min at RT. Acetic acid was removed by two time co-evaporation with ethanol, and the 5'-aminohexyl-L-RNA according to SEQ ID NO: 4 purified by precipitation in ethanol (yield: 220 OD, 60% pure). The product was taken up into 1 M sodium acetate, pH 8.0, and desalted by means of size exclusion chromatography by a Sephadex G10 column or by Vivaspin 3000 (Vivascience, Hannover, Germany).

The L-RNA 5'-amino modified in such a manner (530 OD, 60% pure) was prepared in aqueous universal buffer according to Theorell and Stenhagen (33 mM sodiumcitrate, 33 mM sodium phosphate, 57 mM sodium borate, pH 7.5) (7.5 ml), warmed to 37° C., DMF (5 ml) added, and powdery N-hydroxysuccinimidyl (NHS)-activated ester of branched 40,000 Da poly(ethylen)glycol was added in portions (2 eq every 45 min, alltogether 18 eq). The progress of the reaction was monitored by analytical gelectrophoresis (8% polyacrylamide, 8.3 M urea) or analytical ion exchange HPLC. The raw product was purified initially by ion exchange HPLC from excess PEG (Source Q; solvent A: 10 mM sodium hydrogencarbonate, pH 7.5, solvent B: 10 mM sodium hydrogencarbonate, pH 7.5, 2 M sodium chloride, loading of the column and elution of free PEG with 5% B; flow rate,20 ml/min; separation and elution of the PEG-L-RNA conjugate from non-reacted L-RNA with a gradient up to 35% B over 20 column volumes; flow rate 50 ml/min), subsequently desalted by ultrafiltration (Labscale TFF System, Millipore). By lyophilisation the desired product was obtained as a white powder (254 OD, 48% (80% related to the purity of the starting product)).

Analogously, further L-nucleic acids including the sequence according to SEQ ID NO:1 were linked with different PEG (linear 10,000 Dalton, linear 20,000 Dalton, branched 20,000 Dalton, linear 35,000 Dalton), and purified.

EXAMPLE 10

Activity Test of a GnRH Binding DNA Spiegelmer in vivo in Male Orchidectomised Rats Male rats were orchidectomised, whereby the LH level of the rats increased steadily during the following eight days due to the missing testosteron feedback signal. On day 8 the PEG-GnRH DNA spiegelmer (NOX 1255) was administered subcutaneously to five rats (100 mg/kg). Blood samples were taken on day 0 (prior to the orchidectomy), on day 8 (0 hours prior to s.c. application of the GnRH spiegelmer), as well as 0.5 h, 1.5 h, 3 h, 6 h 24 h post s.c. application and the respective LH level determined using radioimmunoassay (RIA). In parallel, only the vehicle (PBS buffer, pH 7.4) as a negative control was administered s.c. to five male orchidectomised rats, and the standard antagonist Cetrorelix (100 µg/kg) s.c. as a positive control to five male orchidectomised rats. The result is shown in FIG. 29.

The LH levels are lowered in the GnRH DNA spiegelmer group (in FIG. 29 depicted as circles) and reach their lowest point after 1.5 h, and stay on for around 3 h. This reduction is comparable to non-orchidectomised rats and those rats, respectively, treated with Cetrorelix (standard antagonist). Six hours after GnRH DNA spiegelmer dose the LH levels increase slowly and reach the level of the untreated control group within 24 h.

Thus the biological effect of the GnRH DNA spiegelmer is observable over a period of 3 hours, while the PEGylated GnRH DNA spiegelmer is active over a period of 24 hours (see example 5).

The references given in the following correspond to the citations, provided with superscript numbers, given herein.

LITERATURE

1. Bragg, P. D. & Hou, C. Subunit composition, function, and spatial arrangement in the Ca2+- and Mg2+-activated adenosine triphosphatases of *Escherichila coli* and *Salmonella typhimurium. Arch Biochem Biophys* 167, 311 (1975).
2. Lomant, A. J. & Fairbanks, G. Chemical probes of extended biological structures: synthesis and properties of the cleavable protein cross-linking reagent [35S] dithio bis(succinimidyl propionate) .*J Mol Biol* 104, 243-261 (1976).
3. Buter, J. & Kellogg, R. M. Synthesis of macrocyclic and medium ring dithio compounds using cesium thiolates. *J Chem. Soc. Chem. Commun.,* 466-468 (1980).
4. Buter, J. & Kellogg, R. M. Synthesis of sulfur-containing macrocycles using cesium thiolates. *J Org. Chem.* 46, 4481-4485 (1981).
5. Kennedy, R. J. & Stock, A. M. The oxidation of organic substances by potassium peroxymonosulfates. *J Org. Chem.* 25, 1901-1906 (1960).
6. Huang, Z., Schneider, K. C. & Benner, S. A. Oligonucleotide analogs with dimethylenesulfide, -sulfoxide, and -sulfone groups replacing pholsphodiester linkages. *Methods Mol Biol* 20, 315-353 (1993).
7. Connolly, B. A. & Rider, P. Chemical synthesis of oligonucleotides containing a free sulphydryl group and subsequent attachment of thiol specific probes. *Nucleic Acids Res* 13, 4485-4502 (1985).
8. Smyth, D. G., Blumenfeld, O. O. & Konigsberg, W. Reactions of N-ethylmaleimide with peptides and amino acids. *Biochem J,* 91, 589-595 (1964).
9. Heitz, J. R., Anderson, C. D. & Anderson, B. M. Inactivation of yeast alcohol dehydrogenase by N-alkylmaleimides. *Arch Biochem Biophys* 127, 627-636 (1968).
10. Podhradsky, D., Drobnica, L. & Kristian, P. Reactions of cystine, its derivatives, glutathione coenzyme A, and dihydrolipoic acid with isothiocyanates. *Experientia* 35, 154-155 (1979).
11. Vishnyakova, Golubeva & Glebova. *Russ. Chem. Rev.* 54, 249-261 (1985).
12. Hazzard, Lammiman, Poon, Satchell & Satchell. *J. Chem. Soc. Perkin Trans.* 2, 1029 (1985).
13. Pieken, W. et al. (International Patent, 1998).
14. Mokhir, A. A., Tetzlaff, C. N., Herzberger, S., Mosbacher, A. & Richert, C. Monitored selection of dna-hybrids forming duplexes with capped terminal c:g base pairs. *J Comb Chem* 3, 374-386 (2001).
15. Bischoff, R., Coull, J. M. & Regnier, F. E. Introduction of 5'-terminal functional groups into synthetic oligonucleotides for selective immobilization. *Anal Biochem* 164, 336-344 (1987).
16. Ghosh, S. S. & Musso, G. F. Covalent attachment of oligonucleotides to solid supports; *Nucleic Acids Res* 15, 5353-5372 (1987).
17. Allen, D. J., Darke, P. L. & Benkovic, S. J. Fluorescent oligonucleotides and deoxynucleotide triphosphates: preparation and their interaction with the large (Klenow) fragment of *Escherichia coli* DNA polymerase 1. *Biochemistry* 28, 4601-4607 (1989).
18. Pitha, J., Kociolek, K. & Caron, M. G. Detergents linked to polysaccharides: preparation and effects on membranes and cells. *Eur J Biochem* 94, 11-18 (1979).
19. Elling, L. & Kula, M. R. Immunoaffinity partitioning: synthesis and use of polyethylene glycol-oxirane for coupling to bovine serum albumin and monoclonal antibodies. *Biotechnol Appl Biochem* 13, 354-362 (1991).
20. Wardell. in The chemistry of the thiol group (ed. Patai) 246-251 (Wiley, New York, 1974).
21. Zuckermann, R., Corey, D. & Schutz, P. Efficient methods for attachment of thiol specific probes to the 3'-ends of synthetic oligodeoxyribonucleotides. *Nucleic Acids Res* 15, 5305-5321 (1987).
22. Teare, J. & Wollenzien, P. Specificity of site directed psoralen addition to RNA. *Nucleic Acids Res* 17, 3359-3372 (1989).
23. Ghosh, S. S., Kao, P. M. & Kwoh, D. Y. Synthesis of 5'-oligonucleotide hydrazide derivatives and their use in preparation of enzyme-nucleic acid hybridization probes. *Anal Biochem* 178, 43-51 (1989).
24. Ivanovskaya, M. G., Gottikh, M. B. & Shabarova, Z. A. Modifikation of oligo(poly)nucleotide phosphomonoester groups in aqueous solution. *Nucleosides Nucleotides* 6, 913-934 (1987).

25. Ralph, R. K., Young, R. J. & Khorana, H. G. The labeling of phosphomonoester end groups in amino acid acceptor ribonucleic acids and its use in the determination of nucleotide sequences. *J. Am. Chem. Soc.* 84, 1490-1491 (1962).
26. Chu, B. C., Wahl, G. M. & Orgel, L. E. Derivatization of unprotected polynucleotides. *Nucleic Acids Res* 11, 6513-6529 (1983).
27. Shabarova, Z. A. Chemical development in the design of oligonucleotide probes for binding to DNA and RNA. *Biochimie* 70, 1323-34 (1988).

The features of the invention disclosed in the description above, the claims as well as the figures may be essential individually as well as in any combination for the realisation of the invention in its different embodiments.

The invention claimed is:

1. A modified L-nucleic acid, comprising an L-nucleic acid part and a non-L-nucleic acid part, wherein the L-nucleic acid part is conjugated with the non-L-nucleic acid part, wherein the conjugate of the L-nucleic acid part with the non-L-nucleic acid part has an increased retention time in an organism compared to an L-nucleic acid comprising only the L-nucleic acid part, wherein said L-nucleic acid part is a spiegelmer, and wherein said L-nucleic acid part comprises SEQ ID NO:1.

2. The modified L-nucleic acid of claim 1, wherein the non-L-nucleic acid part has a molecular weight of more than about 300 Da.

3. The modified L-nucleic acid of claim 1, wherein the modified L-nucleic acid has a molecular weight to 500,000 Da.

4. The modified L-nucleic acid of claim 1, wherein the L-nucleic acid part has a molecular weight to 50,000 Da.

5. The modified L-nucleic acid of claim 1, wherein the non-L-nucleic acid part is Linked to the L-nucleic acid part via a functional group of the L-nucleic acid part, wherein the functional group is selected from the group consisting of terminal and non-terminal phosphates, terminal and non-terminal sugar portions, natural and non-natural purine bases, and natural and non-natural pyrimidine bases.

6. The modified L-nucleic acid of claim 5, wherein the linkage of the non L-nucleic acid part with the L-nucleic acid part is via the 2'-OH—, 3'-OH—, 5'-OH-group or a derivative therefrom, or one or more sugars of the L-nucleic acid part.

7. The modified L-nucleic acid of claim 5, wherein the linkage is via at least one of the positions 5 or 6 of a pyrimidine base.

8. The modified L-nucleic acid of claim 5, wherein the linkage is via a purine base.

9. The modified L-nucleic acid of claim 5, wherein the linkage is at one or more of the exocyclic amine groups, endocyclic amine groups or keto groups of a purine or pyrimidine base or a basic position.

10. The modified L-nucleic acid of claim 1, wherein the non-L-nucleic acid part is selected from the group consisting of linear poly (ethylene) glycol, branched poly (ethylene) glycol, hydroxyethyl starch, a peptide, a protein, a polysaccharide, a sterol, polyoxypropylene, polyoxyamidate, poly (2-hydroxyethyl)-L-glutamine and polyethylene glycol.

11. The modified L-nucleic acid of claim 1, wherein a linker is arranged between the L-nucleic acid part and the non-L-nucleic acid part.

12. The modified L-nucleic acid of claim 11, wherein said linker is a 6-aminohexylphosphate at the 5'-OH end.

13. The modified L-nucleic acid of claim 12, wherein polyethylene glycol is coupled to the free amine of the aminohexyiphosphate linker.

14. A pharmaceutical composition comprising the modified L-nucleic acid of claim 1 and a pharmaceutically acceptable carrier, excipient or diluent.

15. A method for preparing the modified L-nucleic acid of claim 1, comprising the steps:

(a) providing an L-nucleic acid comprising SEQ ID NO: 1;

(b) providing a non-L-nucleic acid;

(c) reacting the L-nucleic acid from (a) and the non-L-nucleic acid from (b); and (d) optionally isolating the modified L-nucleic acid obtained in step (c) wherein the L-nucleic acid part is a Spiegelmer.

16. The method of claim 15, wherein the L-nucleic acid in step (a) comprises a linker.

17. The method of claim 15, wherein after providing the L-nucleic acid instep (a), a linker is provided.

18. The modified L-nucleic acid of claim 2, wherein the molecular weight is more than about 20,000 Da.

19. The modified L-nucleic acid of claim 18, wherein the molecular weight is more than 40,000 Da.

20. The modified L-nucleic acid of claim 8, wherein said linkage occurs at the 8 position.

* * * * *